US010376676B2

(12) United States Patent
Ishida

(10) Patent No.: US 10,376,676 B2
(45) Date of Patent: *Aug. 13, 2019

(54) CATHETER ASSEMBLY

(71) Applicant: TERUMO KABUSHIKI KAISHA, Shibuya-ku, Tokyo (JP)

(72) Inventor: Masahiro Ishida, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 140 days.

This patent is subject to a terminal disclaimer.

(21) Appl. No.: 15/220,870

(22) Filed: Jul. 27, 2016

(65) Prior Publication Data

US 2016/0331939 A1    Nov. 17, 2016

Related U.S. Application Data

(63) Continuation of application No. PCT/JP2015/051776, filed on Jan. 23, 2015.

(30) Foreign Application Priority Data

Jan. 29, 2014 (JP) ................. 2014-014122

(51) Int. Cl.
A61M 25/06    (2006.01)
A61M 25/09    (2006.01)
A61M 5/158    (2006.01)

(52) U.S. Cl.
CPC .... *A61M 25/0606* (2013.01); *A61M 25/0612* (2013.01); *A61M 25/0631* (2013.01); *A61M 25/09041* (2013.01); *A61M 5/158* (2013.01)

(58) Field of Classification Search
CPC .......... A61M 25/0612; A61M 25/0631; A61M 25/0606; A61M 2005/1585
See application file for complete search history.

(56) References Cited

U.S. PATENT DOCUMENTS 5,873,864 A * 2/1999 Luther ............. A61M 25/0068
604/175
2003/0083620 A1* 5/2003 Luther ............. A61M 25/0606
604/164.07
(Continued)

FOREIGN PATENT DOCUMENTS

JP        10-503094 A    3/1998
WO    WO 95/11710 A1    5/1995

OTHER PUBLICATIONS

International Search Report (PCT/ISA/210) dated Apr. 21, 2015, by the Japanese Patent Office as the International Searching Authority for International Application No. PCT/JP2015/051776.
(Continued)

*Primary Examiner* — Emily L Schmidt
(74) *Attorney, Agent, or Firm* — Buchanan Ingersoll & Rooney PC

(57) ABSTRACT

A catheter assembly is disclosed, which includes a needle support portion that supports an inner needle through a catheter on the leading end side beyond a catheter hub. The needle support portion has a pair of support arms openable and closeable in a left and right direction, and a restraining portion capable of restraining the pair of arms in a closed state and releasing the restraint. A needle hub has an extension portion extending in a leading end direction beyond the catheter hub. A coupling portion between each of the pair of support arms and the extension portion is positioned on the leading end side beyond a base end of the catheter hub.

16 Claims, 27 Drawing Sheets

(56) References Cited

U.S. PATENT DOCUMENTS

| | | | |
|---|---|---|---|
| 2006/0100585 A1* | 5/2006 | Wang | A61M 25/0631 604/177 |
| 2010/0210934 A1* | 8/2010 | Belson | A61M 25/0105 600/371 |
| 2011/0282285 A1 | 11/2011 | Blanchard et al. | |
| 2011/0306933 A1 | 12/2011 | Djordjevic et al. | |
| 2012/0010577 A1* | 1/2012 | Liska | A61M 25/0606 604/272 |
| 2013/0150784 A1 | 6/2013 | Rodriguez Lelis et al. | |
| 2018/0133438 A1* | 5/2018 | Hulvershorn | A61M 25/0113 |

OTHER PUBLICATIONS

Written Opinion (PCT/ISA/237) dated Apr. 21, 2015, by the Japanese Patent Office as the International Searching Authority for International Application No. PCT/JP2015/051776.

* cited by examiner

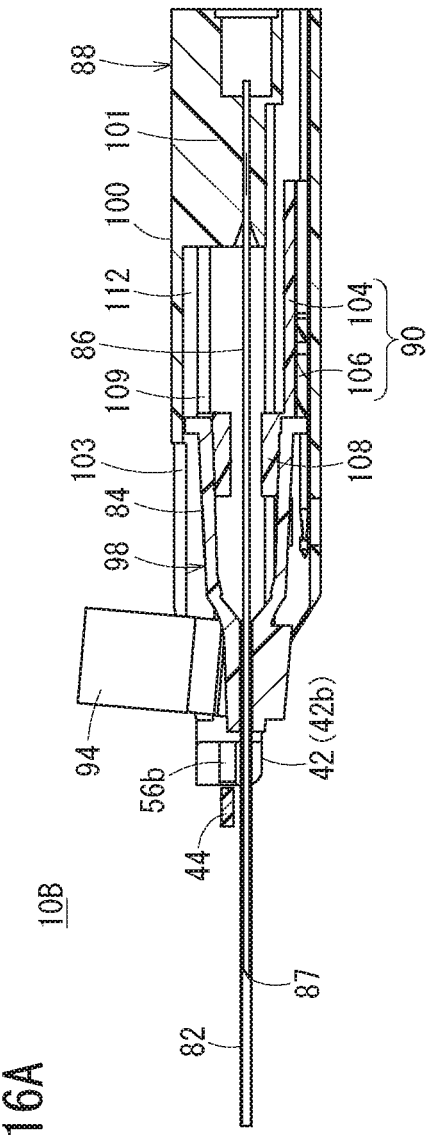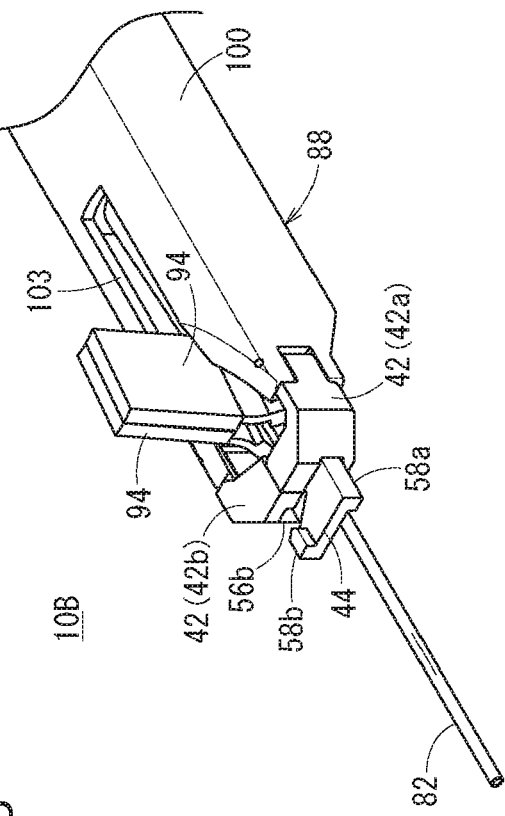

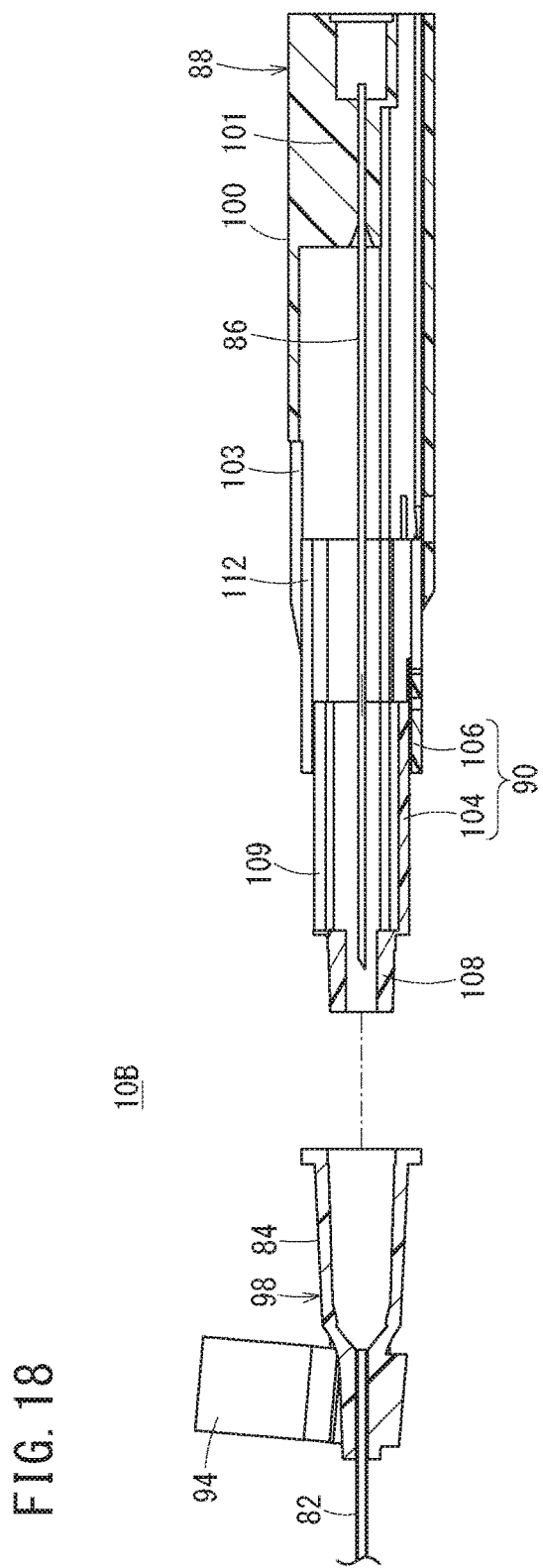

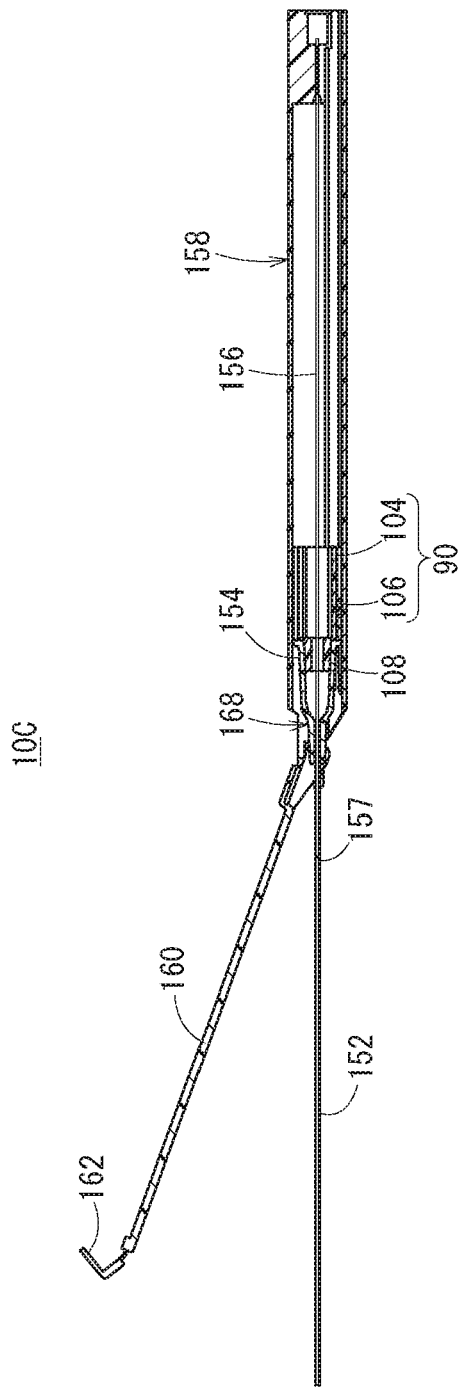

CATHETER ASSEMBLY

CROSS-REFERENCES TO RELATED APPLICATIONS

This application is a continuation of International Application No. PCT/JP2015/051776 filed on Jan. 23, 2015, which claims priority to JP 2014-014122 filed on Jan. 29, 2014, the entire content of which are incorporated herein by reference.

TECHNICAL FIELD

The present disclosure relates to a catheter assembly that punctures a blood vessel and is detained, for example, upon performing a transfusion to a patient.

BACKGROUND ART

Conventionally, when a transfusion is performed to a patient, for example, a catheter assembly is used. This kind of catheter assembly can include a hollow catheter, a catheter hub adhered to a base end of the catheter, an inner needle inserted into the catheter and having a sharp needlepoint at a leading end, and a needle hub adhered to a base end of the inner needle. In a case where a transfusion is performed to a patient by using the catheter assembly, the catheter with the inner needle punctures a blood vessel of the patient, and the inner needle is evulsed from the catheter while the catheter is puncturing the patient after the puncture. Next, a connector provided at an end portion of a transfusion tube is coupled to a base end of the catheter hub, and a transfusion material is supplied into the blood vessel of the patient through the transfusion tube, the catheter hub, and the catheter.

It is known that a unit for supporting the inner needle through the catheter is provided in the above catheter assembly in order to inhibit or prevent deflection of the inner needle upon the puncture (for example, refer to JP 10-503094 W and US 2011/0282285 A).

JP 10-503094 W discloses that openable and closeable two arms extending in a leading end direction are provided on a needle hub, and the two arms are open before use and do not support an inner needle. A user pinches the arms upon a puncture so that the puncture can be performed while deflection of the inner needle is being inhibited. After the puncture, the user weakens the pinching force with respect to the two arms so that the two arms open and a catheter hub can move forward.

US 2011/0282285 A discloses that openable and closeable two arms extending in a leading end direction are provided on a needle hub, and, before use, the two arms have been closed, support an inner needle through a catheter, and have been restrained in a closed state by a restraining portion. In use, when the restraining portion moves forward, the restraint of the restraining portion is released. After that, when the two arms open in an upper and lower direction, a catheter hub becomes movable forward. The two arms have been coupled to each other at a base end portion of a catheter assembly through a hinge portion.

The catheter assembly described in JP 10-503094 W requires an operation in which the user strengthens and weakens the pinching force with respect to the two arms in order to perform support with respect to the inner needle and release from the support. Thus, the operation is complicated.

In the catheter assembly described in US 2011/0282285 A, since the two arms for supporting the inner needle open in the upper and lower direction, a protruding length of the inner needle from the arms is made long in order to avoid interference with skin of the patient. Thus, the inner needle easily deflects. Upon a puncture, the vicinity of leading ends of the arms in order to easily perform the puncture is held. After the restraint with respect to the arms has been released, it can be necessary to hold the vicinity of base portions of the arms (a base end portion of the catheter assembly) instead of the vicinity of leading ends of the arms in order to open the arms. Thus, the operation can be complicated.

SUMMARY OF INVENTION

A catheter assembly is disclosed, which is capable of being easily operated and inhibiting or preventing deflection of an inner needle effectively upon a puncture.

A catheter assembly according to the present disclosure can include: a catheter; a catheter hub fixed to a base end portion of the catheter; an inner needle having a needlepoint, inserted into the catheter; a needle hub coupled to the inner needle; and a needle support portion for supporting the inner needle through the catheter on a leading end side beyond the catheter hub. The needle support portion has a pair of support arms openable and closeable in a left and right direction, and a restraining portion capable of restraining the pair of support arms in a closed state and releasing the restraint. The needle hub has an extension portion extending in a leading end direction beyond the catheter hub. A coupling portion between each of the pair of support arms and the extension portion is positioned on the leading end side beyond a base end of the catheter hub.

With the above configuration of the present disclosure, since the pair of support arms supports the inner needle upon a puncture, the deflection of the inner needle upon the puncture can be inhibited or prevented, and a stable puncture can be performed. In particular, according to the present disclosure, an adjustment of gripping force by a user does not perform the support of the inner needle and the release of the support, but a function of the restraining portion performs the restraint with respect to the pair of support arms and the release of the restraint. Thus, the operation is relatively simple. Since the pair of support arms that opens in the left and right direction, has no interference with skin of a patient, there is no need for extra lengthening of the inner needle in order to avoid the interference. Thus, the deflection of the inner needle can be effectively inhibited. Furthermore, since the support arms are provided on the leading end side beyond a base end of the catheter hub, for example, gripping the extension portion provided on the leading end side beyond the base end of the catheter hub without changing the hold of the grip, can sequentially perform a puncture operation and a forward movement operation of the catheter hub by the same hand. Therefore, excellent operability can be acquired.

According to an exemplary embodiment, the above catheter assembly may further include: a bending first engaging groove provided in one of the support arms; a bending second engaging groove provided in the other of the support arms; a first restraining protrusion capable of engaging with the first engaging groove, provided on the restraining portion; and a second restraining protrusion capable of engaging with the second engaging groove, provided on the restraining portion. With this configuration, the needle support portion can be constituted so as to be compact.

According to an exemplary embodiment, in the above catheter assembly, when the restraining portion is positioned at a first position, the first restraining protrusion may engage with the first engaging groove and the second restraining protrusion may engage with the second engaging groove. When the restraining portion is positioned at a second position, the second restraining protrusion may separate from the second engaging groove in a state where the restraining portion has been held by the one of the support arms, the one including the first engaging groove. With this configuration, after the restraint with respect to the pair of support arms has been released, since the restraining portion moves with one of the pair of support arms, a forward movement of the catheter hub is not prevented.

According to an exemplary embodiment, in the above catheter assembly, the second restraining protrusion may protrude to a side opposite to a side on which the inner needle is present. With this configuration, when the one of a pair of support arms holding the restraining portion opens, the second restraining protrusion can be prevented from being hooked on the inner needle.

According to an exemplary embodiment, in the above catheter assembly, the extension portion and each of the support arms may be coupled so as to be rotatable through a hinge structure having a first structure and a second structure. The first structure may be provided on one of the extension portions and each of the support arms, and has a plurality of coupling pieces facing each other and a recess portion formed between the plurality of coupling pieces. The second structure may be provided on the other of the extension portion and each of the support arms, and has a coupling protruding portion disposed in the recess portion. With this configuration, since the first structure and the second structure are in relationship of the mutual engagement, unsteadiness of the hinge structure can be effectively inhibited.

According to an exemplary embodiment, in the above catheter assembly, a support hole for supporting the inner needle may be formed between the pair of support arms in the closed state. A contact surface between the pair of support arms may be shifted in the left and right direction with respect to a center of the inner needle supported by the support hole. With this configuration, even when force in an upper and lower direction acts on the inner needle, the inner needle barely comes off the pair of support arms that has been closed.

According to an exemplary embodiment, in the above catheter assembly, the restraining portion may be slidable with respect to the pair of support arms. In accordance with a forward movement of the catheter hub or a forward movement of a guide wire operating portion for operating a guide wire inserted into the inner needle, the catheter hub, a hub operating portion provided on the catheter hub, or the guide wire operating portion may press the restraining portion so as to release the restraint with respect to the pair of support arms. With this configuration, since the restraint with respect to the pair of support arms is automatically released in response to a forward movement operation with respect to a predetermined member, there is no need for an independent release operation. Therefore, excellent operability can be acquired.

According to an exemplary embodiment, in the above catheter assembly, the restraining portion may be provided as a part of a hub operating portion for operating the catheter hub or a part of a guide wire operating portion for operating a guide wire inserted in the inner needle. The restraint with respect to the pair of support arms may be released upon a forward movement of the hub operating portion or a forward movement of the guide wire operating portion. With this configuration, since the restraint with respect to the pair of support arms is automatically released in response to an operation with respect to the hub operating portion or the guide wire operating portion, there is no need for an independent release operation. Therefore, excellent operability can be acquired.

A catheter assembly is disclosed, comprising: a catheter; a catheter hub fixed to a base end portion of the catheter; an inner needle having a needlepoint, inserted into the catheter; a needle hub coupled to the inner needle, the needle hub has an extension portion extending in a leading end direction beyond the catheter hub; a needle support portion for supporting the inner needle through the catheter on a leading end side beyond the catheter hub, the needle support portion having a pair of rotatable support arms, and a restraining portion capable of restraining the pair of support arms; and a coupling portion between each of the pair of support arms and the extension portion is positioned on the leading end side beyond a base end of the catheter hub.

According to the catheter assembly of the present disclosure, the operation is relatively simple and the deflection of the inner needle upon a puncture can be effectively inhibited.

BRIEF DESCRIPTION OF THE DRAWINGS

FIG. 16A is a longitudinal-sectional view of the catheter assembly illustrated in FIG. 11 in a state where a catheter hub has moved forward partway through.

FIG. 16B is a perspective view of the catheter assembly illustrated in FIG. 11 in the state where the catheter hub has moved forward partway through.

FIG. 18 is a longitudinal-sectional view of the catheter assembly illustrated in FIG. 11 in a state where the catheter hub and the protector have been separated from each other.

FIG. 25 is a longitudinal-sectional view of a state where the hub operating portion has further moved forward from the state of FIG. 24A.

DETAILED DESCRIPTION

Preferred embodiments regarding a catheter assembly according to the present disclosure, will be given and described below with reference to the drawings.

Figure 1:
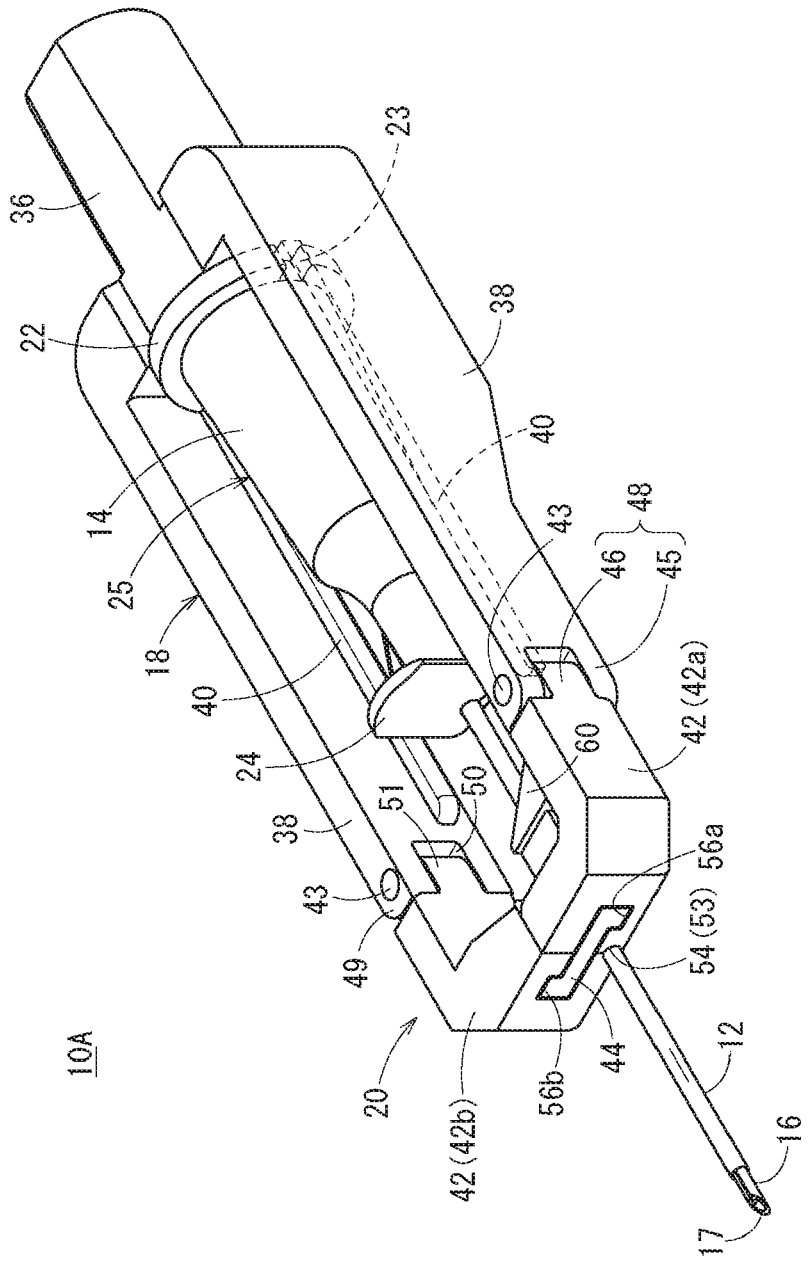
FIG. 1 is a perspective view of a catheter assembly according to a first embodiment of the present disclosure.
Figure 2:
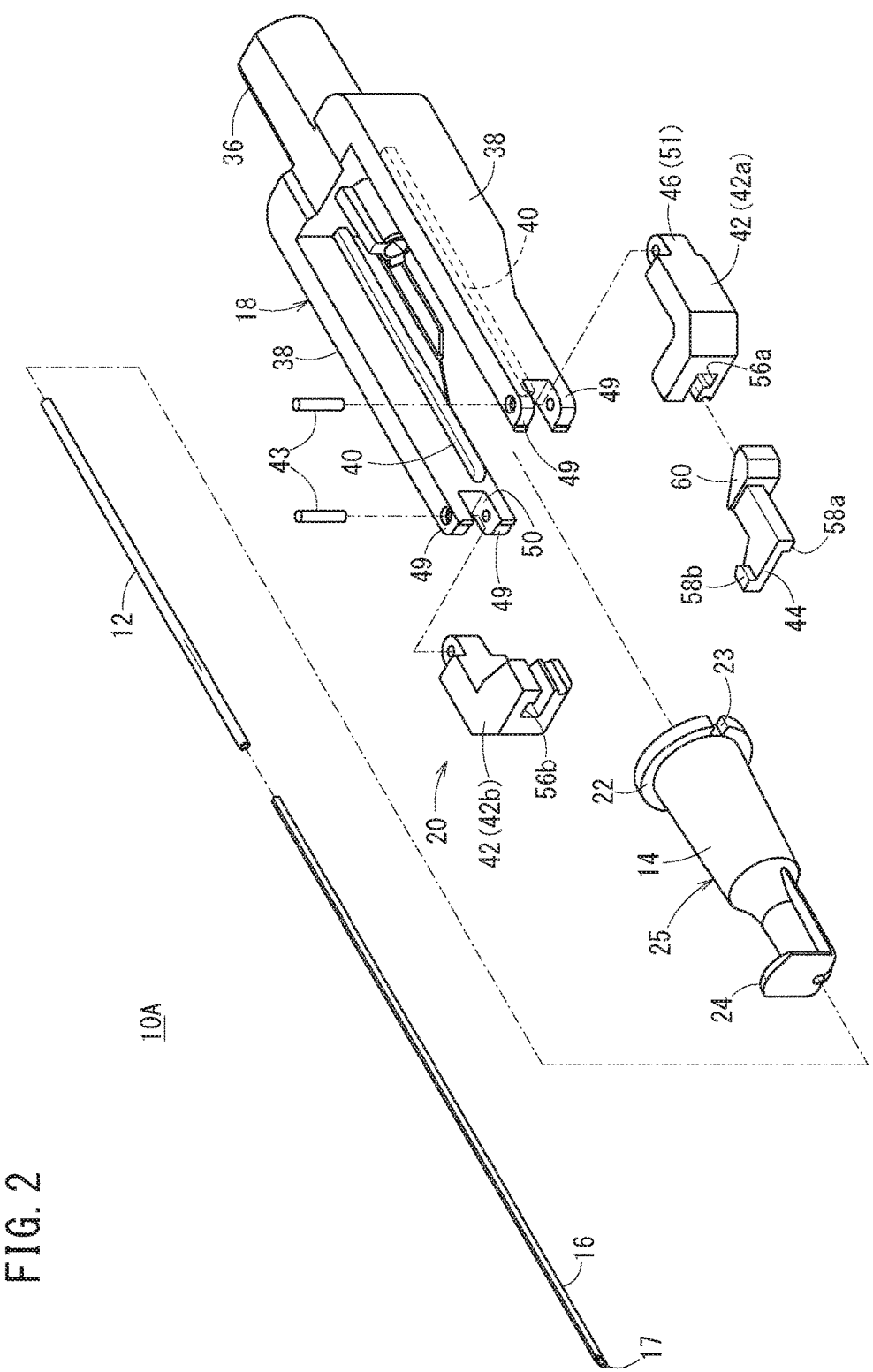
FIG. 2 is an exploded perspective view of the catheter assembly illustrated in FIG. 1.
Figure 3:
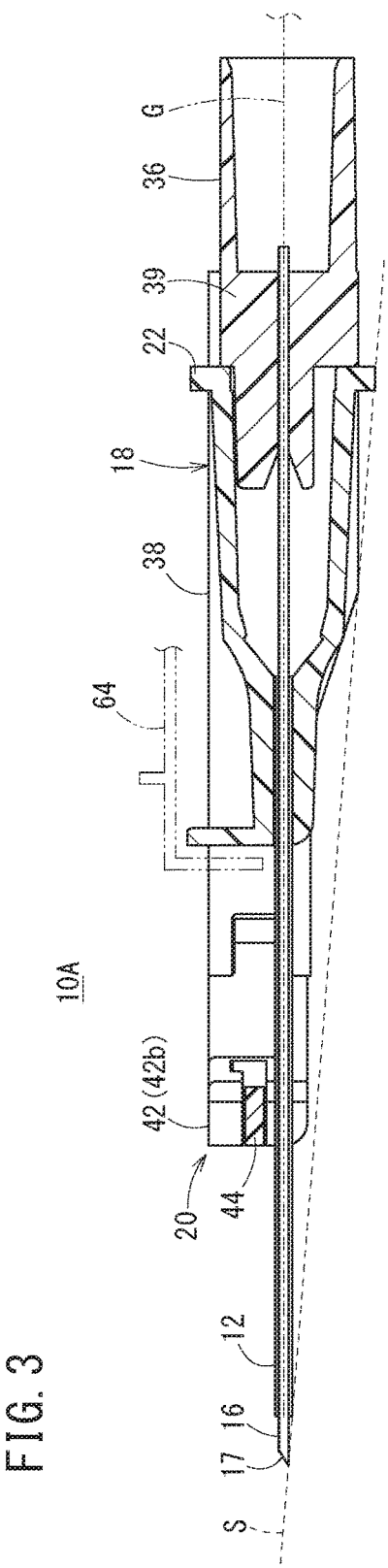
FIG. 3 is a longitudinal-sectional view of the catheter assembly illustrated in FIG. 1.

FIG. 1 is a perspective view of an entire configuration of a catheter assembly 10A according to a first embodiment of the present disclosure. FIG. 2 is an exploded perspective view of the catheter assembly 10A. FIG. 3 is a longitudinal-sectional view of the catheter assembly 10A.

The catheter assembly 10A can include a tubular catheter 12 functioning as an outer needle, a catheter hub 14 coupled to the side of a base end of the catheter 12, a tubular inner needle 16 having a sharp needlepoint 17 at a leading end and insertable into the inside of the catheter 12, a needle hub 18 coupled to the inner needle 16, and a needle support portion 20 for inhibiting or preventing deflection of the inner needle 16 upon a puncture.

With the catheter assembly 10A, a user (for example, a medical doctor or a nurse) grips and operates the needle hub 18 so that a leading end portion of the needle hub 18 punctures a blood vessel of a patient. The catheter assembly 10A has a double tubular structure in which the inner needle 16 has been inserted into the catheter 12 and the inner needle 16 has protruded from a leading end of the catheter 12 by a predetermined length in an initial state before use (before a puncture to the patient).

The catheter assembly 10A in the initial state can include one assembly having the double tubular structure of the catheter 12 and the inner needle 16, the catheter hub 14, the needle hub 18, and the needle support portion 20 combined, and is integrally operable.

The catheter 12 is a tubular member that has been formed so as to have a predetermined length, with a small diameter and flexibility. A resin material and, in particular, a soft resin material are preferable as examples of a constituent material of the catheter 12. In this case, for example, fluororesins, such as polytetrafluoroethylene (PTFE), ethylene-tetrafluoroethylene copolymer (ETFE), and perfluoroalkoxy fluoropolymer (PFA), olefin resins, such as polyethylene and polypropylene, or a mixture thereof, polyurethane, polyester, polyamide, polyether nylon resin, and a mixture of the olefin resin and ethylene-vinyl acetate copolymer, are provided. The catheter 12 may include a resin having transparency so that the entire or partial inside of the catheter can be visually ascertained.

The catheter hub 14 is coupled and fixed to the base end of the catheter 12. A flange portion 22 protruding outward and extending in a circumferential direction, is provided on a base end of the catheter hub 14. A cutout 23 is provided on each of the right side and the left side of the flange portion 22.

The catheter hub 14 is provided with a hub operating portion 24 for operating the catheter hub 14. As illustrated in FIG. 1, the hub operating portion 24 of the present illustrated example is a tab protruding upward from a leading end of the catheter hub 14, and can be integrally formed with respect to the catheter hub 14. The hub operating portion 24 may be constituted as a component separated from the catheter hub 14, and may be attachable to and detachable from the catheter hub 14 In accordance with an exemplary embodiment, the user touches and grips or presses the hub operating portion 24 so that the catheter hub 14 can be operated in an axial direction. Note that a position at which the hub operating portion 24 is provided is not limited to the leading end of the catheter hub 14, and may be provided between the leading end and the base end of the catheter hub 14.

Hereinafter, a member including the catheter 12, the catheter hub 14, and the hub operating portion 24, will be referred to as a "catheter member 25".

Upon the use of the catheter assembly 10A, the catheter hub 14 is exposed on skin of the patient, stuck, and detained on the skin with a dressing material or a tape in a state where the catheter 12 has punctured the blood vessel. The above catheter hub 14 preferably can include a material harder than the catheter 12. Examples of the constituent material of the catheter hub 14 that can be preferably used include, but are not particularly limited to, thermoplastic resins, such as polypropylene, polycarbonate, polyamide, polysulfone, polyarylate, and methacrylate-butylene-styrene copolymer.

The inner needle 16 is a tubular member having rigidity capable of puncturing the skin of the patient in FIGS. 1 and 2. The inner needle 16 is formed sufficiently longer than the catheter 12. In the initial state of the catheter assembly 10A, the needlepoint 17 protrudes from a leading end opening of the catheter 12 by a predetermined length. In addition, in the initial state, the inner needle 16 has a midway part in the longitudinal direction inserted into the inside of the catheter hub 14, and has the side of the base end held by the needle hub 18.

Examples of a constituent material of the inner needle 16 include metal materials, such as stainless steel, aluminum or an aluminum alloy, titanium or a titanium alloy.

The needle hub 18 has a hub body 36 disposed in series with the catheter hub 14 and an extension portion 38 extending from the hub body 36 in a leading end direction in the initial state. The hub body 36 has an inner needle holding portion 39 that fixes and holds a base end portion of the inner needle 16.

According to the present embodiment, a pair of extension portions 38 faces each other along the inner needle 16 over both sides of the inner needle 16 and the catheter hub 14, one of the pair of extension portions 38 being provided on the right side of the hub body 36, the other being provided on the left side of the hub body 36. The extension portions 38 extend to the leading end side beyond the base end of the catheter hub 14 in the initial state of the catheter hub 14. That is, leading ends of the extension portions 38 are positioned on the leading end side beyond the leading end of the catheter hub 14. The extension portions 38 are formed so as to be appropriate in size (thickness, length). Thus, the user can easily grip and operate the catheter assembly 10A upon the use of the catheter assembly 10A.

An inside surface of each of the pair of extension portions 38 facing each other can include a guide protrusion 40 extending in an axial direction of the inner needle 16 provided thereon. The left and right guide protrusions 40 are inserted into the left and right cutouts 23 provided on the flange portion 22 of the catheter hub 14, respectively. Accordingly, the catheter hub 14 is stably supported by the needle hub 18 in the initial state. In addition, rotation of the catheter hub 14 with respect to the needle hub 18 can be prevented so that the hub operating portion 24 can be held upward. Upon moving the catheter hub 14 forward with respect to the needle hub 18, the catheter hub 14 can be smoothly moved forward and operated due to a guide function of the guide protrusions 40.

Next, the needle support portion 20 will be described. The needle support portion 20 supports the inner needle 16 through the catheter 12 on the leading end side beyond the catheter hub 14 in the initial state of the catheter assembly 10A. The needle support portion 20 is provided movable with respect to the needle hub 18 in order to change from a first state of supporting the inner needle 16 to a second state of releasing the support with respect to the inner needle 16 and allowing the catheter hub 14 to pass.

According to the present embodiment, specifically, the needle support portion 20 has a pair of support arms 42 openable and closeable and a restraining portion 44 capable of restraining the pair of support arms 42 in a closed state and also releasing the restraint. Hereinafter, in a case where one and the other of the pair of support arms 42 are distinguished from each other and described, the one will be indicated as a "support arm 42a" and the other will be indicated as a "support arm 42b".

Each of the pair of support arms 42 is rotatably coupled to each of the extension portions 38 through each of a pair of support pins 43. In the present illustrated example, each of the pair of support pins 43 has an axis in an upper and lower direction. The pair of support arms 42 supported by the pair of support pins 43 is openable and closeable in a left and right direction. In the initial state, a coupling portion between each of the pair of support arms 42 and each of the pair of extension portions 38, is positioned on the leading end side beyond the base end of the catheter hub 14.

Each of the extension portions 38 and each of the support arms 42 are coupled so as to be rotatable through a hinge structure 48 having a first structure 45 and a second structure 46. According to the present embodiment, the first structure 45 is provided at a leading end of each of the extension portions 38 and the second structure 46 is provided at a base end of each of the support arms 42. The first structure 45 has a plurality of coupling pieces 49 spaced apart in the upper and lower direction and facing each other, and a recess portion 50 formed between the plurality of coupling pieces 49. The second structure 46 has a coupling protruding portion 51 disposed in the recess portion 50. The support pin 43 is inserted into the coupling protruding portion 51 and the two coupling pieces 49 on each of the left side and the right side. Note that, according to a modification, the first structure 45 may be provided at the base end of each of the support arms 42 and the second structure 46 may be provided at the leading end of each of the extension portions 38.

Each of the support arms 42 has a support groove 53 for holding the inner needle 16 in a state where the pair of support arms 42 has been closed, provided thereon. In the state where the pair of support arms 42 has been closed, the two support grooves 53 form a support hole 54 for supporting the inner needle 16 (inner needle 16 inserted into the catheter 12). In the initial state of the catheter assembly 10A, the support hole 54 extends in a direction in which the inner needle 16 extends.

In accordance with an exemplary embodiment, one of the support arms 42 has a bending engaging groove 56a provided thereon and the other has a bending engaging groove 56b provided thereon when viewed from the front side in the closed state. Each of the engaging grooves 56a and 56b passes through each of the support arms 42 in a longitudinal direction. The one engaging groove 56a (hereinafter, referred to as a "first engaging groove 56a") and the other engaging groove 56b (hereinafter, referred to as a "second engaging groove 56b) mutually bend in opposite directions. In accordance with an exemplary embodiment, the first engaging groove 56a bends downward and the second engaging groove 56b bends upward.

Note that, as illustrated in FIG. 3, in a case where a puncture at a small angle is performed to a skin S of a patient, a lower portion of each of the support arms 42 may be at least trimmed so that the support arms 42 does not interfere with the skin S.

The restraining portion 44 is disposed slidable with respect to the pair of support arms 42. The restraining portion 44 is pressed by the catheter hub 14 in accordance with a forward movement of the catheter hub 14 so that the restraint with respect to the pair of the support arms 42 is released.

In accordance with an exemplary embodiment, the restraining portion 44 has a first restraining protrusion 58a engaging with the first engaging groove 56a so as to be slidable and a second restraining protrusion 58b engaging with the second engaging groove 56b so as to be slidable. In the present illustrated example, the first restraining protrusion 58a and the second restraining protrusion 58b mutually protrude in opposite directions so as to fit to shapes of the first engaging groove 56a and the second engaging groove 56b provided on the pair of support arms 42, respectively. When the restraining portion 44 is positioned at an initial position (a backward position), the first restraining protrusion 58a and the second restraining protrusion 58b of the restraining portion 44 engage with the first engaging groove 56a and the second engaging groove 56b of the pair of support arms 42, respectively. Accordingly, the pair of support arms 42 is restrained in the closed state.

The second restraining protrusion 58b separates from the second engaging groove 56b of the other of a pair of support arms 42 in the leading end direction in accordance with a movement of the restraining portion 44 in the leading end direction. When the second restraining protrusion 58b separates from the second engaging groove 56b, the restraint of the restraining portion 44 with respect to the pair of support arms 42 is released and the pair of support arms 42 becomes expansible. Note that, even after the second restraining protrusion 58b has separated from the second engaging groove 56b, engagement between the first restraining protrusion 58a and the first engaging groove 56a is retained so that the restraining portion 44 is held by the support arm 42a.

Figure 4:
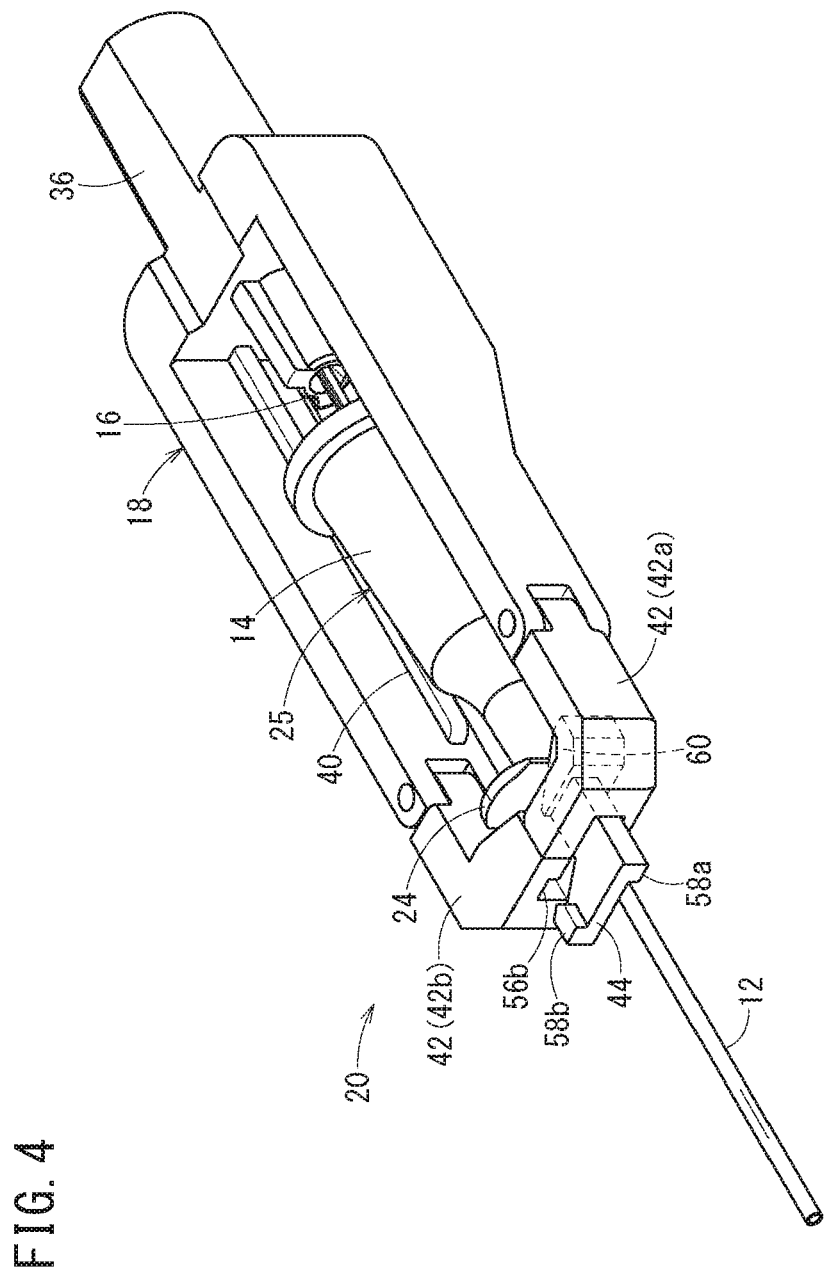
FIG. 4 is a perspective view of the catheter assembly illustrated in FIG. 1 in a state where restraint with respect to a pair of support arms has been released.

In a state where the second restraining protrusion 58b has separated from the second engaging groove 56b, the second restraining protrusion 58b protrudes to the side opposite to the side on which the inner needle 16 is present (refer to FIG. 4). Accordingly, when the support arms 42 open in a state where the inner needle 16 has bended to the side of the restraining portion 44, the inner needle 16 is prevented from being hooked on the second restraining protrusion 58b. Note that, according to a modification, the second restraining protrusion 58b may protrude to the side on which the inner needle 16 is present. In this case, a bending shape of the second engaging groove 56b to be provided to the support arm 42b, is formed so as to be in a direction in which the second restraining protrusion 58b protrudes.

A base end of the restraining portion 44 can include a portion to be pressed 60 provided thereat. Upon a forward movement of the catheter hub 14 with respect to the needle hub 18, the leading end of the catheter hub 14 pressed the portion to be pressed 60 so that the restraining portion 44 moves forward with respect to the pair of support arms 42. A surface of the portion to be pressed 60 facing the catheter hub 14 can include a taper that inclines so as to be displaced outward in the left and right direction as going in a base end direction, provided thereon.

The catheter assembly 10A according to the first embodiment is basically constituted as described above. Functions and effects of the catheter assembly 10A will be described below.

As illustrated in FIGS. 1 and 3, the catheter assembly 10A in the initial state is in a state to be described below. The inner needle 16 has been inserted into the catheter 12 and the needlepoint 17 has protruded from the leading end of the catheter 12 by the predetermined length. The catheter hub 14 has been positioned on the side of a base end so as to be maximum with respect to the needle hub 18. One of the extension portions 38 is present on the right side of the catheter hub 14 and the other of the extension portions 38 is present on the left side. The side of a leading end of the inner needle holding portion 39 of the needle hub 18 has been inserted into the base end of the catheter hub 14. The restraining portion 44 has been positioned at the backward position in a movable range. The pair of support arms 42 has been restrained in the closed state by the restraining portion 44. The inner needle 16 has been held by the pair of support arms 42 in the closed state through the catheter 12.

In the use of the catheter assembly 10A, a user (for example, a medical doctor or a nurse) grips the needle hub 18 and punctures a blood vessel of a patient with the catheter 12 and the inner needle 16. In this case, the inner needle 16 has been supported by the support hole 54 formed between the pair of support arms 42 in the closed state, through the catheter 12, so that deflection of the inner needle 16 is inhibited upon the puncture. Accordingly, a stable puncture can be performed relatively easily.

After the puncture, a finger hooks the hub operating portion 24 protruding upward from the catheter hub 14, and presses the hub operating portion 24 in the leading end direction. Accordingly, the catheter hub 14 and the catheter 12 that have been coupled to the hub operating portion 24, move in the leading end direction with respect to the needle hub 18. Thus, an insertion length of the catheter 12 into the blood vessel increases.

As illustrated in FIG. 4, the hub operating portion 24 presses the restraining portion 44 in the leading end direction in accordance with the forward movement of the catheter hub 14. Accordingly, the restraining portion 44 moves in the leading end direction with respect to the pair of support arms 42, and the second restraining protrusion 58b separates from the second engaging groove 56b. The second restraining protrusion 58b separates from the second engaging groove 56b so that the restraint of the restraining portion 44 with respect to the pair of support arms 42 is released and the pair of support arms 42 becomes expansible.

Figure 5:
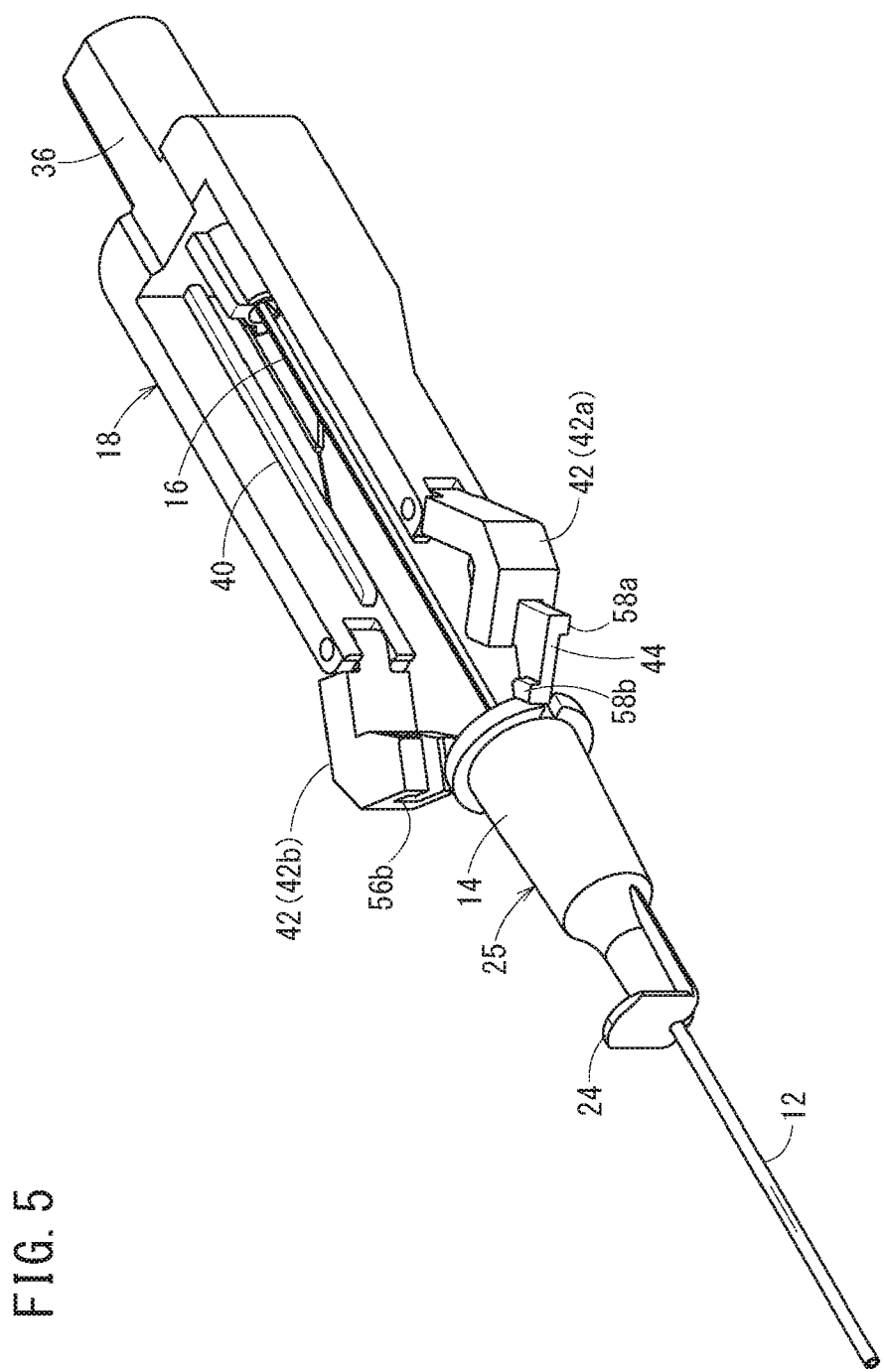
FIG. 5 is a perspective view of the catheter assembly illustrated in FIG. 1 in a state where a catheter member has further moved forward from the state illustrated in FIG. 4.
Figure 6:
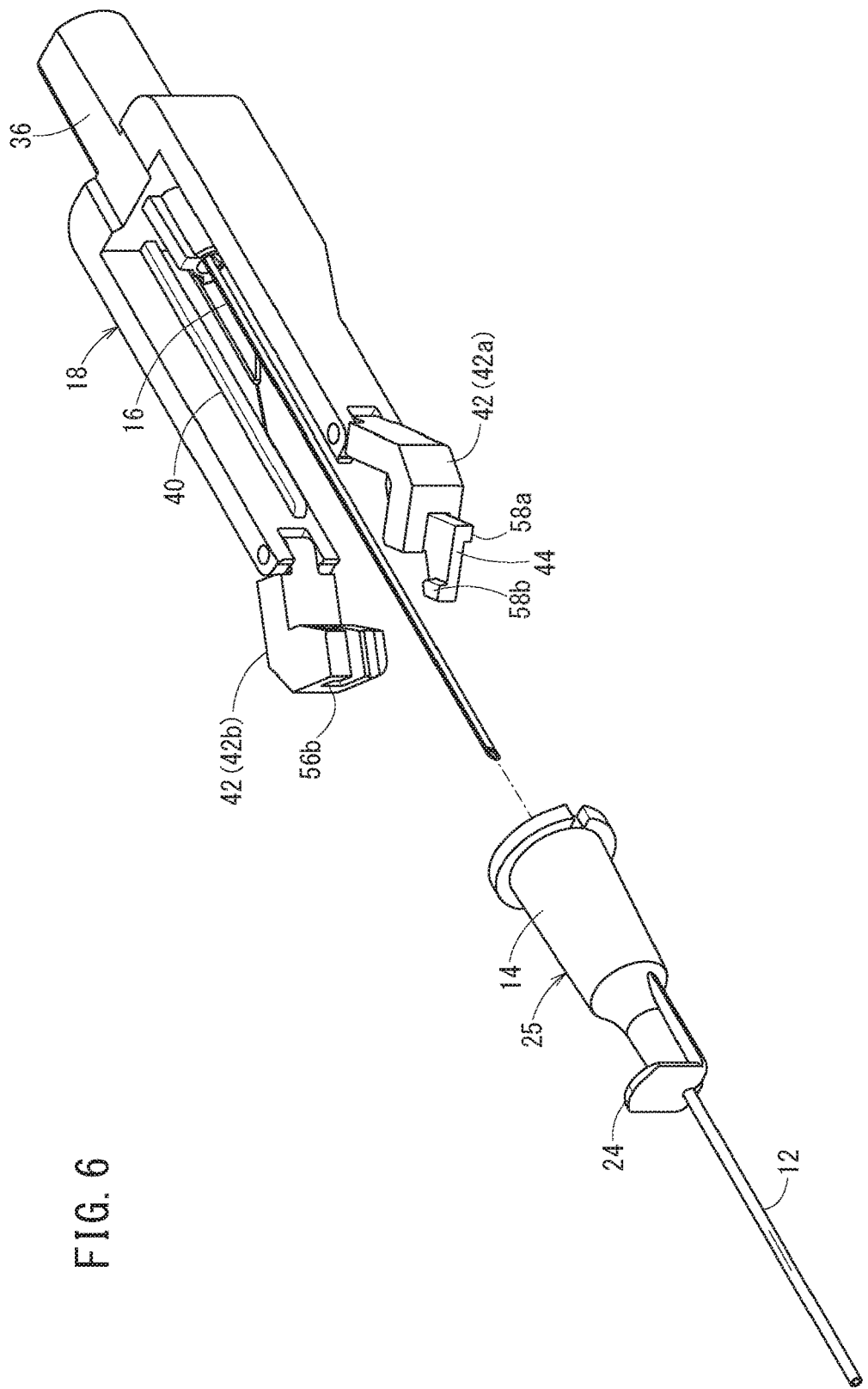
FIG. 6 is a perspective view of the catheter assembly illustrated in FIG. 1 in a state where an inner needle has been evulsed from a catheter.

After that, when the catheter hub 14 further moves forward, the pair of support arms 42 is pressed from the rear side by the hub operating portion 24 and the catheter hub 14 and expands as illustrated in FIG. 5. In this manner, the needle support portion 20 supports the inner needle 16 in the initial state so as to inhibit the deflection of the inner needle 16 upon the puncture. Meanwhile, after the puncture, the pair of support arms 42 opens so as to prevent interference with the catheter hub 14.

After the catheter 12 has been inserted into the blood vessel by a predetermined length, the needle hub 18 is next pulled in the base end direction in a state where a position of the catheter member 25 has been held. Accordingly, the inner needle 16 moves in the base end direction inside the catheter member 25. The inner needle 16 is shortly and completely evulsed from the catheter member 25 as illustrated in FIG. 5. As a result, a state where only the catheter member 25 out of the catheter assembly 10A has been detained on the side of the patient, can be acquired.

After the inner needle 16 has been evulsed from the catheter member 25, the catheter hub 14 is fixed to the patient with, for example, a dressing material or a tape. A connector of a transfusion tube, not illustrated, is coupled to the side of the base end of the catheter hub 14, and supply of a transfusion material (for example, a medical fluid) to the patient through the transfusion tube is performed.

As described above, the catheter assembly 10A according to the first embodiment is capable of inhibiting the deflection of the inner needle 16 upon a puncture and performing a stable puncture since the pair of support arms 42 supports the inner needle 16 upon the puncture.

In accordance with an exemplary embodiment, according to the present disclosure, an adjustment of gripping force by the user does not perform the support of the inner needle 16 and the release of the support, but the function of the restraining portion 44 performs the restraint with respect to the pair of support arms 42 and the release of the restraint. Thus, the operation is relatively simple.

Since the pair of support arms 42 that opens in the left and right direction has no interference with the skin S of the patient, there is no need for extra lengthening the inner needle 16 in order to avoid the interference. Thus, the deflection of the inner needle 16 can be effectively inhibited.

Furthermore, since the support arms 42 are provided on the leading end side beyond the base end of the catheter hub 14, for example, gripping the extension portions 38 provided on the leading end side beyond the base end of the catheter hub 14 without changing the hold of the grip, can sequentially perform a puncture operation and a forward movement operation of the catheter hub 14 by the same hand. Therefore, excellent operability can be acquired.

In accordance with an exemplary embodiment, according to the first embodiment, since the restraint with respect to the pair of support arms 42 is automatically released in response to a forward movement operation with respect to the hub operating portion 24, there is no need for an independent release operation. Therefore, excellent operability can be acquired.

According to the first embodiment, a structure is disclosed in which the first and second restraining protrusions 58a and 58b provided on the restraining portion 44 engage with the first and second engaging grooves 56a and 56b provided on the pair of support arms 42, respectively. Therefore, the needle support portion 20 can be constituted so as to be compact.

Furthermore, according to the first embodiment, when the restraining portion 44 has been positioned at a forward movement position, the second restraining protrusion 58b separates from the second engaging groove 56b in a state where the restraining portion 44 has been held by the support arm 42a including the first engaging groove 56a provided thereon. With this configuration, since the restraining portion 44 moves with one of the pair of support arms 42 after the restraint with respect to the pair of support arms 42 has been released, the forward movement of the catheter hub 14 is not prevented.

In accordance with an exemplary embodiment, since the second restraining protrusion 58b protrudes in the side opposite to the side on which the inner needle 16 is present, when the one of the pair of support arm 42a that holds the restraining portion 44 opens, the second restraining protrusion 58b can be prevented from being hooked on the inner needle 16.

According to the first embodiment, each of the extension portions 38 and each of the support arms 42 are coupled so as to rotatable through the hinge structure 48 having the first structure 45 and the second structure 46. The first structure 45 and the second structure 46 are in relationship of the mutual engagement. Thus, unsteadiness of the hinge structure 48 can be inhibited.

In accordance with an exemplary embodiment, in the above configuration, the hub operating portion 24 presses the restraining portion 44 so that the restraint with respect to the pair of support arms 42 is released. Instead of this type of configuration, the catheter hub 14 may press the restraining portion 44 so that the restraint with respect to the pair of support arms 42 may be released. Alternatively, the catheter assembly 10A may further include a guide wire G inserted into the inner needle 16 and a guide wire operating portion 64 for operating the guide wire G, the guide wire operating portion 64 being coupled to the guide wire G (refer to FIG. 3). In this case, the guide wire operating portion 64 may press the restraining portion 44 in accordance with a forward movement of the guide wire operating portion 64. Thus, the restraint with respect to the pair of support arms 42 may be released.

Figure 7A:
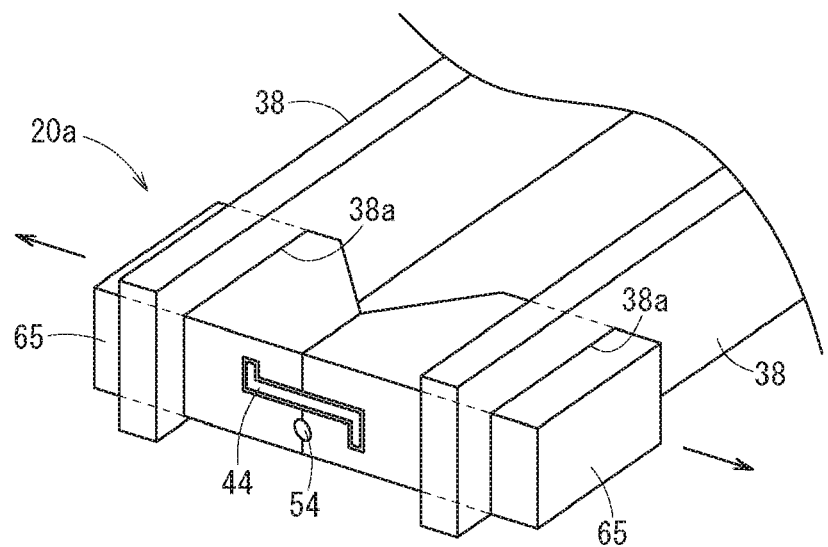
FIG. 7A is a perspective view of a needle support portion according to a first modification.
Figure 7B:
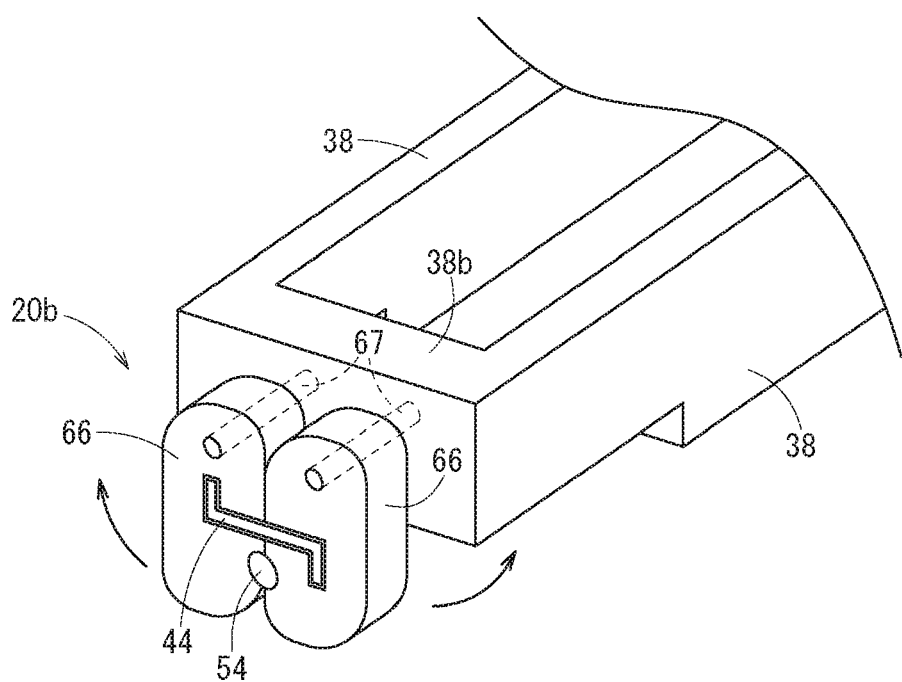
FIG. 7B is a perspective view of a needle support portion according to a second modification.
Figure 8:
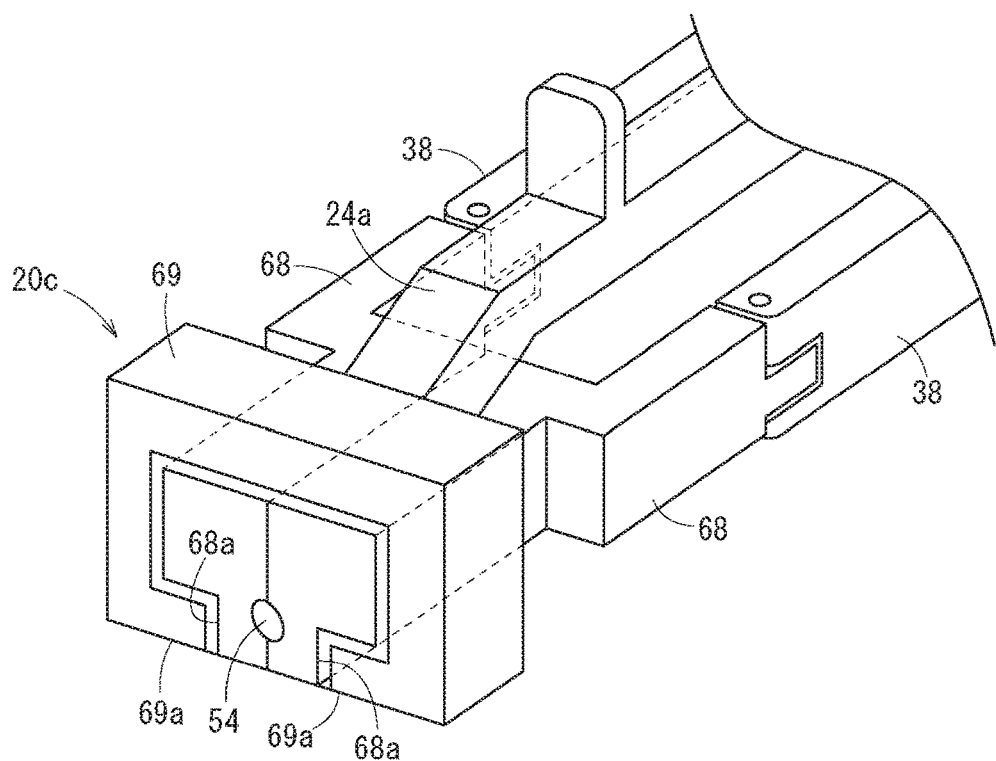
FIG. 8 is a perspective view of a needle support portion according to a third modification.

Instead of the above needle support portion 20, needle support portions 20a to 20c illustrated in FIGS. 7A to 8 may be adopted. Note that the illustrations of the inner needle 16, the catheter 12, and the catheter hub 14 have been omitted in FIGS. 7A to 8.

The needle support portion 20a illustrated in FIG. 7A can include a pair of support arms 65 slidable in a left and right direction with respect to left and right extension portions 38, provided therein. In this case, each of the extension portions 38 has a slide hole 38a for holding each of the support arms 65 to be slidable in the left and right direction, provided therein, for example. With the above configuration in FIG. 7A, the pair of support arms 65 is also openable and closeable in the left and right direction. Therefore, a first state where the inner needle 16 has been supported can change to a second state where the support of the inner needle 16 has been released and the catheter hub 14 has been allowed to pass.

A needle support portion 20b illustrated in FIG. 7B can include a pair of support arms 66 that has been supported so as to be rotatable by a pair of support pins 67 parallel to the axial direction of the inner needle 16. In this case, for example, leading ends of left and right extension portions 38 cam be coupled together, and the pair of support pins 67 is fixed to the coupled portion 38b. With the above configuration in FIG. 7B, the pair of support arms 66 is also openable and closeable in the left and right direction. Therefore, a first state where the inner needle 16 has been supported can change to a second state where the support of the inner needle 16 has been released and the catheter hub 14 has been allowed to pass.

A needle support portion 20c illustrated in FIG. 8 can include a pair of support arms 68 openable and closeable in the left and right direction, and a restraining portion 69 capable of restraining the pair of support arms 68 in a closed state and releasing the restraint. In FIG. 8, the restraining portion 69 is formed so as to have a frame shape surrounding leading end portions of the support arms 68, and is capable of restraining the pair of support arms 68 in a closed state. Instead of the hub operating portion 24, a hub operating portion 24a is provided. The hub operating portion 24a is coupled to the restraining portion 69. When a forward movement operation of the hub operating portion 24a is performed, the restraining portion 69 separates from the pair of support arms 42 in the leading end direction. Thus, the restraint with respect to the pair of support arms 68 is released. Note that, instead of the hub operating portion 24a, a guide wire operating portion may be provided.

Note that, with the configuration in FIG. 8, the restraining portion 69 has been formed so as to have the frame shape surrounding the leading end portions of the support arms 68. Left and right inward protruding ends 69a of the restraining portion 69 enter step portions 68a provided at leading end lower portions of the support arms 68. Due to the above configuration, a structure present below the inner needle 16 can be prevented from increasing in size. In contrast, in a case where the step portions 68a that the left and right inward protruding ends 69a of the restraining portion 69 enter are not provided on the support arms 68, a structure present below the inner needle 16 increases in size and easily interfere with skin of a patient.

Figure 9A:
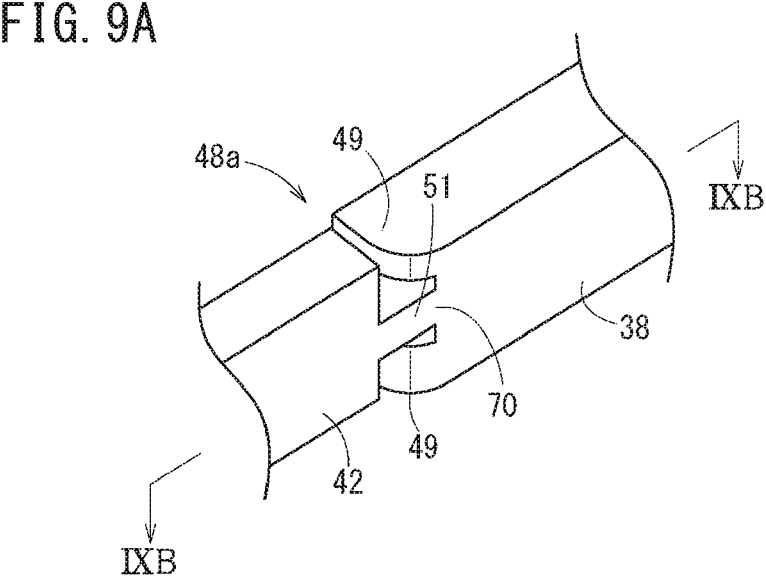
FIG. 9A is a perspective view of a hinge structure according to the first modification.
Figure 9B:
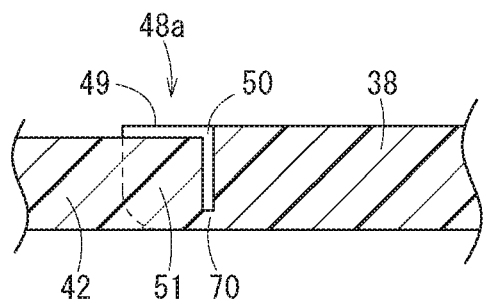
FIG. 9B is a sectional view taken along line IXB-IXB of FIG. 9A.

Instead of the above hinge structure 48, a hinge structure 48a illustrated in FIGS. 9A and 9B may be adopted. Note that FIG. 9B is a sectional view taken along line IXB-IXB of FIG. 9A. In the hinge structure 48a, a support arm 42 and an extension portion 38 are integrally formed through a thin-walled portion 70. In this case, the thin-walled portion 70 functions as a bending portion so that the support arm 42 is rotatable with respect to the extension portion 38.

Figure 9C:
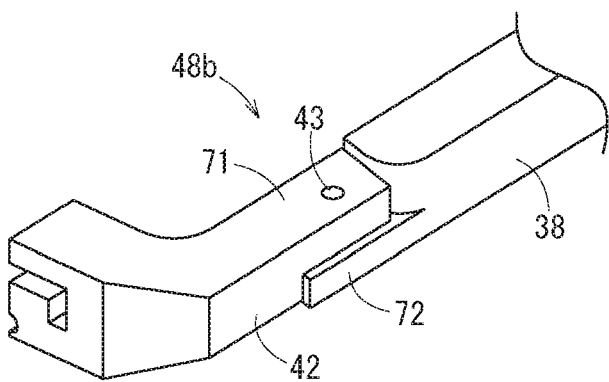
FIG. 9C is a perspective view of a hinge structure according to the second modification.

As a hinge structure 48b illustrated in FIG. 9C, a configuration in which one coupling piece 71 provided at a base end of a support arm 42 and one coupling piece 72 provided at a leading end of an extension portion 38 are coupled with a support pin 43 so as to be rotatable in a state where vertically overlapping with each other, may be adopted. Alternatively, the hinge structure 48b may have a configuration in which the support pin 43 and the support arm 42 have been integrally formed. Instead of using the support pin 43, a configuration in which the support arm 42 and the extension portion 38 have been integrally formed through a thin-walled portion, may be provided.

In the above configuration, each of the support arms 42 can include the support groove 53 provided thereon, and the two support grooves 53 form the support hole 54. Thus, a position of a contact surface between the support arms 42 in the left and right direction is substantially the same as a position of an axis of the inner needle 16 supported by the support hole 54. Accordingly, in a case where predetermined force or more acts on the inner needle 16 in the upper and lower direction, there is a possibility that the inner needle 16 comes off the pair of support arms 42 that has been closed. Therefore, instead of the support hole 54, for example, support holes 54a to 54d illustrated in FIGS. 10A to 10D, respectively, may be adopted. Note that, FIGS. 10A to 10D schematically illustrate the restraining portion 44 and the first and second engaging grooves 56a and 56b have been omitted in order to mainly exemplify structures of the support holes 54a to 54d.

Figure 10A:
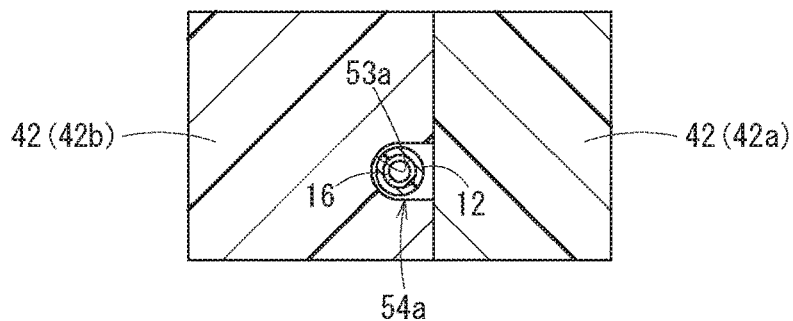
FIG. 10A is a schematic sectional view of a support hole according to the first modification.

The structure of the support hole 54a illustrated in FIG. 10A can include no support groove provided on one support arm 42a and a support groove 53a (a groove deeper than the support groove 53) provided on only the other support arm 42b. In a state where the pair of support arms 42 has been closed, an inner surface of the one support arm 42a and the support groove 53a provided on the other support arm 42b form the support hole 54a. With this structure, a position of a contact surface between the pair of support arms 42 moves in the left and right direction with respect to the center of the inner needle 16 supported by the support hole 54a. Accordingly, even when force in the upper and lower direction acts on the inner needle 16, the inner needle 16 barely comes off the pair of support arms 42 that has been closed.

Figure 10B:
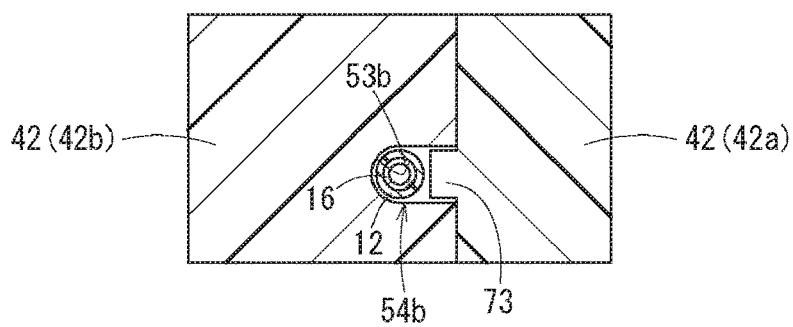
FIG. 10B is a schematic sectional view of a support hole according to the second modification.

The structure of the support hole 54b illustrated in FIG. 10B can include a protruding portion 73 protruding inward (the side of the other support arm 42b), provided on one support arm 42a, and a support groove 53b further deep provided on the other support arm 42b. In a case where the pair of support arms 42 has been closed, the protruding portion 73 is inserted into the support groove 53b, and the protruding portion 73 and the support groove 53b form the support hole 54b. With this structure, a position of a contact surface between the pair of support arms 42 also moves in the left and right direction with respect to the center of the inner needle 16 supported by the support hole 54b. Thus, the inner needle 16 barely comes off.

Figure 10C:
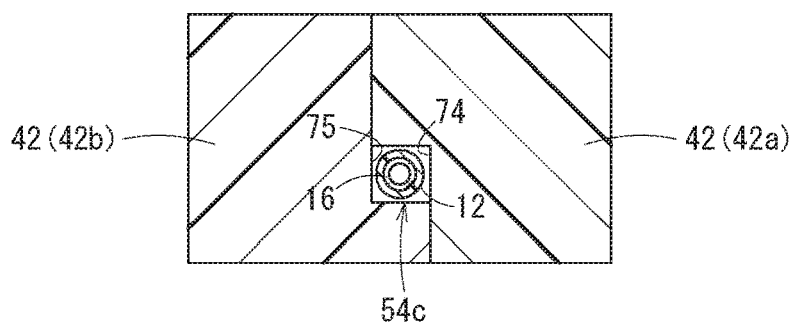
FIG. 10C is a schematic sectional view of a support hole according to the third modification.

The structure of the support hole 54c illustrated in FIG. 10C can include step portions 74 and 75 provided on an inner surface of one support arm 42a. In a state where a pair of support arms 42 has been closed, the left and right step portions 74 and 75 form the support hole 54c. With this structure, a position of a contact surface between the pair of support arms 42 also moves in the left and right direction with respect to the center of the inner needle 16 supported by the support hole 54c. Thus, the inner needle 16 barely comes off.

Figure 10D:
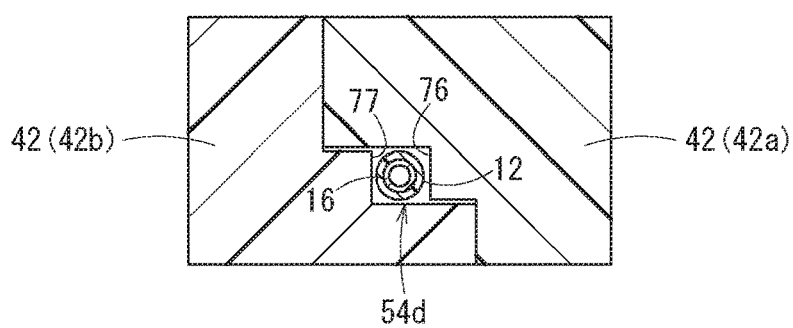
FIG. 10D is a schematic sectional view of a support hole according to a fourth modification.

The structure of the support hole 54d illustrated in FIG. 10D can include stair-shapes 76 and 77 having multiple steps provided on respective inner surfaces of support arms 42. In a state where the pair of support arms 42 has been closed, the left and right stair-shapes 76 and 77 form the support hole 54d. With this structure, a position of a contact surface between the pair of support arms 42 also moves in the left and right direction with respect to the center of the inner needle 16 supported by the support hole 54d. Thus, the inner needle 16 barely comes off.

Figure 11:
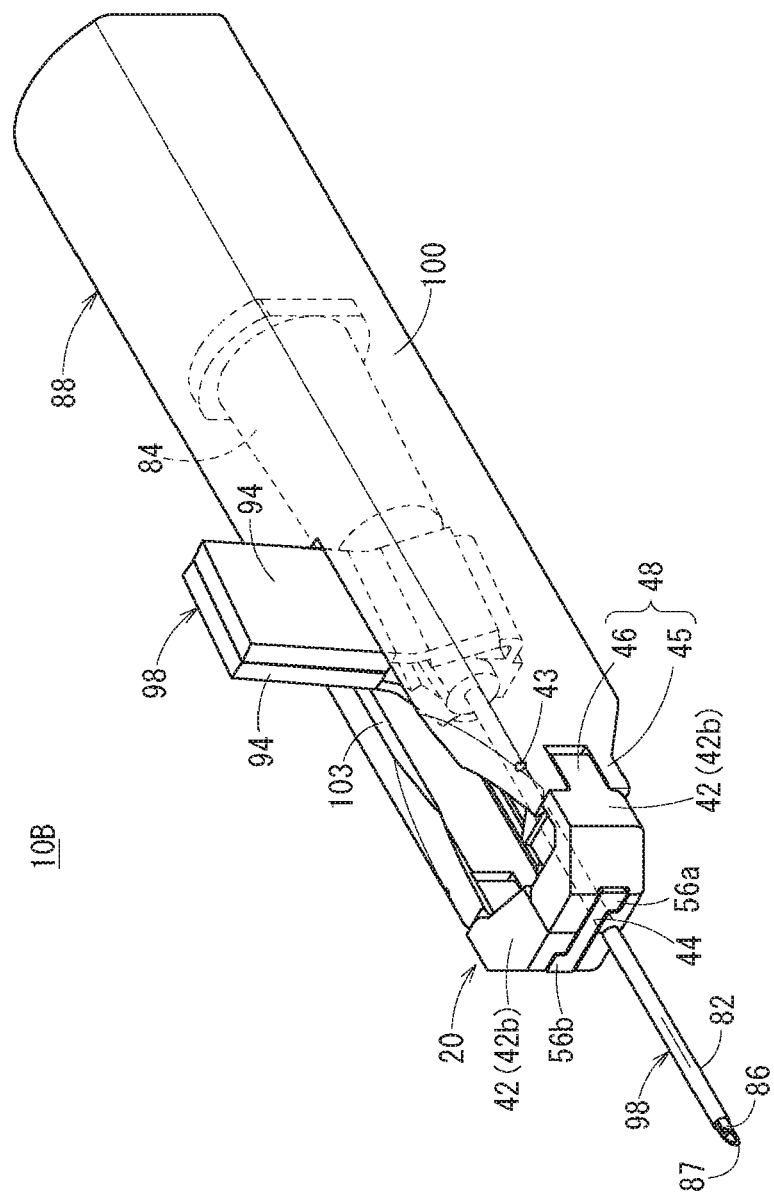
FIG. 11 is a perspective view of a catheter assembly according to a second embodiment of the present disclosure.
Figure 12:
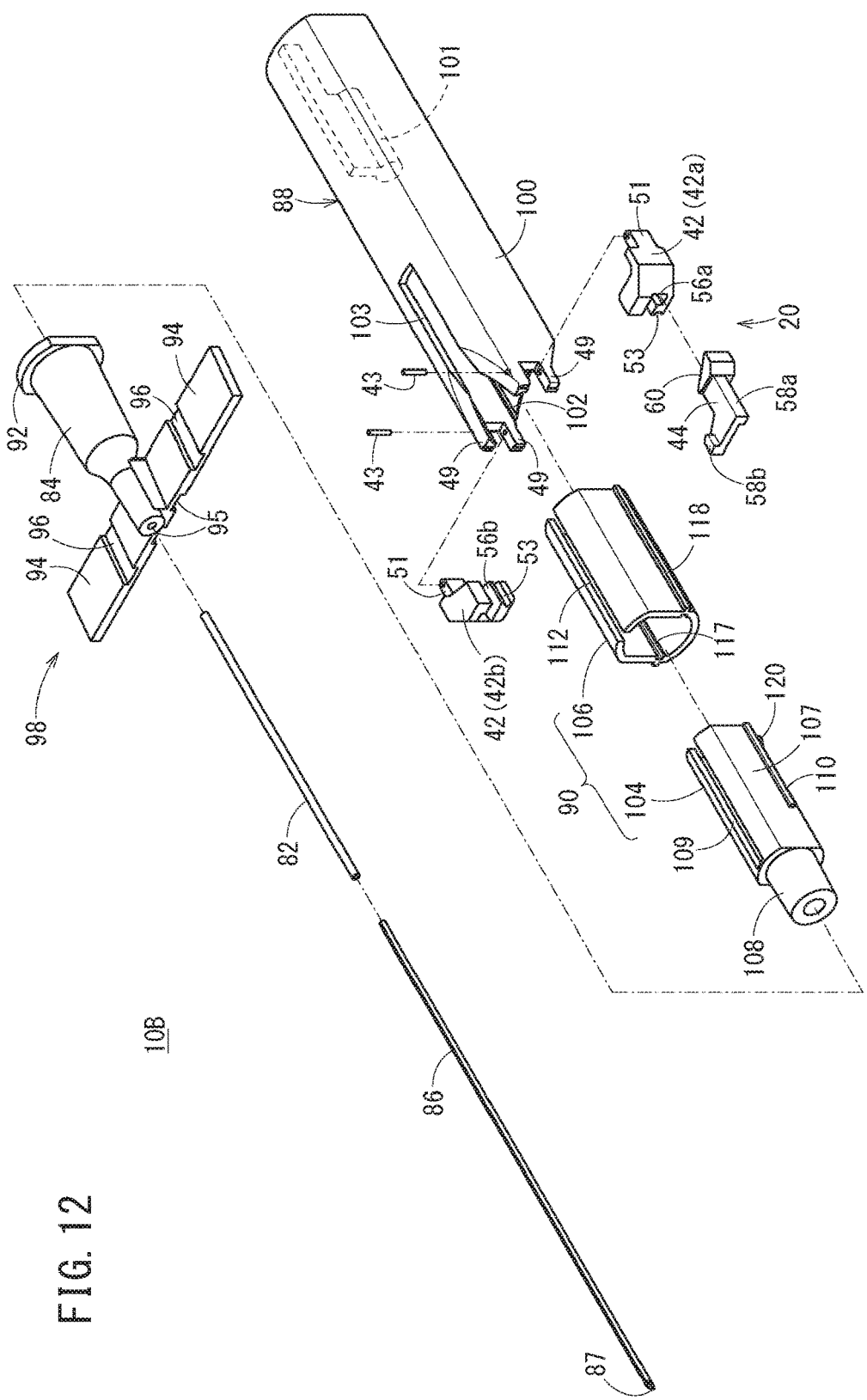
FIG. 12 is an exploded view of the catheter assembly illustrated in FIG. 11.
Figure 13:
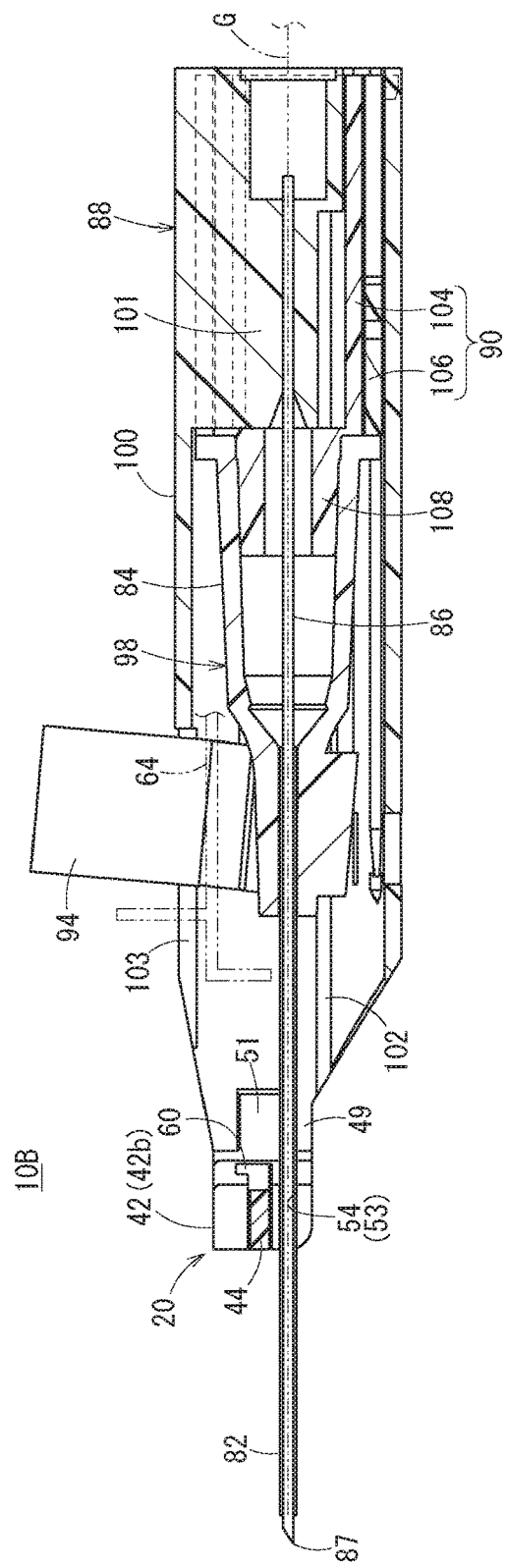
FIG. 13 is a longitudinal-sectional view of the catheter assembly illustrated in FIG. 11.

FIG. 11 is a perspective view of a catheter assembly 10B according to a second embodiment of the present disclosure. FIG. 12 is an exploded perspective view of the catheter assembly 10B. FIG. 13 is a longitudinal-sectional view of the catheter assembly 10B. Note that, in the catheter assembly 10B according to the second embodiment, elements having functions and effects the same as or similar to those of the catheter assembly 10A according to the first embodiment, are denoted with the same reference signs, and the duplicate descriptions thereof will be omitted.

The catheter assembly 10B can include a tubular catheter 82 having flexibility, a catheter hub 84 coupled to the side of a base end of the catheter 82, a tubular inner needle 86 having a sharp needlepoint 87 on a leading end and insertable into the inside of the catheter 82, a needle hub 88 coupled to the inner needle 86, a protector 90 that covers the needlepoint 87 of the inner needle 86 when the inner needle 86 is evulsed, and a needle support portion 20 for inhibiting deflection of the inner needle 86.

With the catheter assembly 10B, a user (for example, a medical doctor or a nurse) grips and operates the needle hub 88 so that a leading end portion of the needle hub 88 punctures a blood vessel of a patient. The catheter assembly 10B has a double tubular structure in which the inner needle 86 has been inserted into the catheter 82 and the inner needle 86 has protruded from a leading end of the catheter 82 by a predetermined length in an initial state before use (before a puncture to the patient). In the initial state of the catheter assembly 10B, the catheter hub 84 and the needle hub 88 have been coupled through the protector 90.

The catheter assembly 10B in the initial state can include one assembly having the double tubular structure of the catheter 82 and the inner needle 86, the catheter hub 84, the protector 90, and the needle hub 88 combined, and is integrally operable.

The hollow cylindrical catheter hub 84 is coupled and fixed to the base end of the catheter 82. A flange portion 92 protruding outward and extending in a circumferential direction, is provided on a base end of the catheter hub 84.

The catheter hub 84 can include a pair of wings 94 that protrudes in a left and right direction in a natural state, provided thereon. The wings 94 each have flexibility and are foldable so as to overlap with each other. As illustrated in FIG. 12, according to the present embodiment, each of the wings 94 can include a first thin-walled portion 95 provided at a coupling part with the catheter hub 84 and a second thin-walled portion 96 provided on the outside beyond the first thin-walled portion 95. The first thin-walled portion 95 is provided so as to be groove-shaped on the side of a lower surface of each of the wings 94. The second thin-walled portion 96 is provided so as to be groove-shaped on the side of an upper surface of each of the wings 94.

With this configuration, the wings 94 can easily fold upward at parts of the first thin-walled portions 95 and can easily fold in a direction opposite to the first thin-walled portions 95 at parts of the second thin-walled portions 96. As illustrated in FIG. 11, in the initial state of the catheter assembly 10B, outer end portions of the wings 94 are exposed from the needle hub 88. The user touches and grips or presses the wings 94 exposed from the needle hub 88 so that the catheter hub 84 can be operated in an axial direction. That is, the pair of wings 94 functions as an operating portion for operating the catheter hub 84.

Hereinafter, a member including the catheter 82, the catheter hub 84, and the pair of wings 94, will be referred to as a "catheter member 98."

As illustrated in FIG. 13, the inner needle 86 is formed sufficiently longer than the catheter 82. In the initial state of the catheter assembly 10B, the needlepoint 87 protrudes from a leading end opening of the catheter 82 by a predetermined length. In addition, in the initial state, the inner needle 86 has a midway part in the longitudinal direction inserted into the inside of the catheter hub 84, and has the side of the base end held inside the needle hub 88.

As illustrated in FIGS. 12 and 13, the needle hub 88 has an inner needle holding portion 101 holding the base end of the inner needle 86, and an extension portion 100 protruding in a leading end direction beyond the catheter hub 84. The extension portion 100 is included in a housing that houses the catheter hub 84 and the protector 90 in the initial state.

The inner needle holding portion 101 protrudes downward from the center in the left and right direction on the side of a base end of the extension portion 100. A rail groove 102 extending in the axial direction is provided on each of left and right inside surfaces of the extension portion 100.

In the initial state of the catheter assembly 10B, the catheter 82 and the inner needle 86 are exposed from a leading end of the needle hub 88, and the catheter hub 84 and the protector 90 are housed in the needle hub 88. As a result, the leading end of the needle hub 88 protrudes to a midway of the catheter 82. According to the present embodiment, a position of the base end of the catheter hub 84 is positioned on the base end side beyond a position of the center in an axial direction of the needle hub 88, and the leading end of the needle hub 88 is positioned on the leading end side beyond a position of the center in a longitudinal direction of the catheter 82.

As illustrated in FIGS. 11 to 13, a slit 103 that extends in the axial direction of the needle hub 88 and is open on the side of the leading end of the needle hub 88, is formed in the needle hub 88 (specifically, the extension portion 100). According to the present embodiment, the slit 103 can be formed on an upper wall of the needle hub 88. In the initial state of the catheter assembly 10B, the outer end portions of the wings 94 that have been folded and overlap each other protrude upward from the needle hub 88 through the slit 103.

The protector 90 houses the inner needle 86 in accordance with evulsion of the inner needle 86 from the catheter 82 so as to cover the needlepoint 87 of the inner needle 86. As illustrated in FIGS. 12 and 13, the protector 90 has an inner tube 104 fitting to the base end of the catheter hub 84 so as to be separable, and an outer tube 106 in which the inner tube 104 is disposed on the inside thereof, and which is relatively displaceable in the axial direction in a range regulated with respect to the inner tube 104. Upon the evulsion of the inner needle 86 from the catheter 82, the protector 90 extends so as to cover an entire length of the inner needle 86 (refer to FIG. 18).

The inner tube 104 functions to cover the needlepoint 87 of the inner needle 86 in accordance with the evulsion of the inner needle 86 from the catheter 82. The inner tube 104 has a body portion 107 and a leading end fitting portion 108 protruding from the body portion 107 in the leading end direction. An upper wall of the body portion 107 can include a cutout 109 extending in the axial direction, formed thereon. In the initial state, the inner tube 104 is positioned in the base end of the needle hub 88. The inner needle holding portion 101 of the needle hub 88 is inserted into the cutout 109 of the body portion 107. Each of left and right outer surfaces of the body portion 107 can include a rail protrusion 110 extending in the axial direction (refer to FIG. 12) provided thereon.

The leading end fitting portion 108 of the inner tube 104 is formed so as to have a taper shape that decreases in outer diameter as going in the leading end direction. In the initial state, the leading end fitting portion 108 of the inner tube 104 fits into the base end of the catheter hub 84. The inner tube 104 and the catheter hub 84 are coupled due to frictional resistance on a fitting surface.

The outer tube 106 is disposed between the inner tube 104 and the needle hub 88. An upper wall of the outer tube 106 can include a cutout 112 extending in the axial direction, formed thereon. In the initial state, the outer tube 106 is positioned in the base end of the needle hub 88 with the inner tube 104. The inner needle holding portion 101 of the needle hub 88 is inserted into the cutout 112.

A rail groove 117 extending in the axial direction is provided on each of left and right inner surfaces of the outer tube 106. The rail protrusions 110 provided on the inner tube 104 are inserted into the rail grooves 117 provided on the outer tube 106 (refer to FIG. 15). Each of left and right outer surfaces of the outer tube 106 can include a rail protrusion 118 extending in the axial direction provided thereon. The rail protrusions 118 provided on the outer tube 106 are inserted into the rail grooves 102 provided on the extension portion 100 (refer to FIG. 15).

Figure 14:
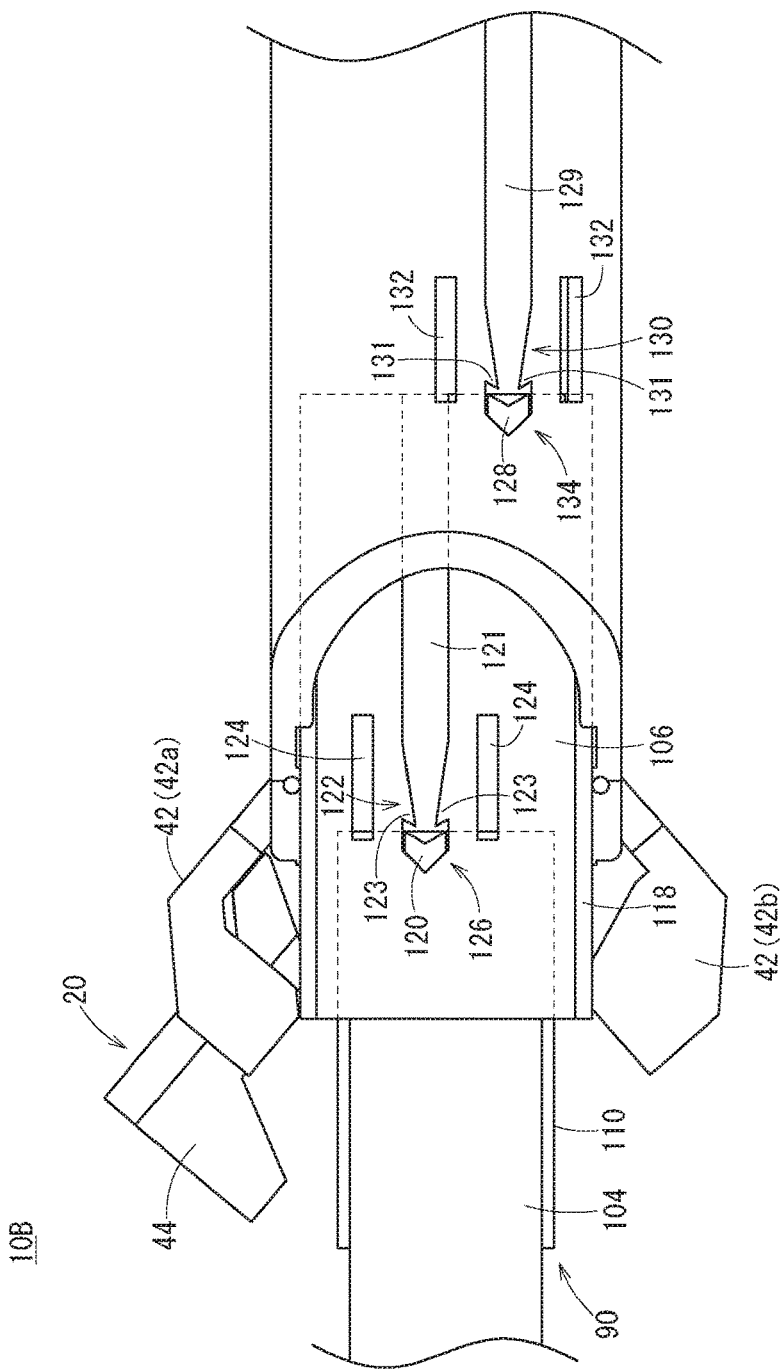
FIG. 14 is a partially omitted rear view of the catheter assembly illustrated in FIG. 11.
Figure 15:
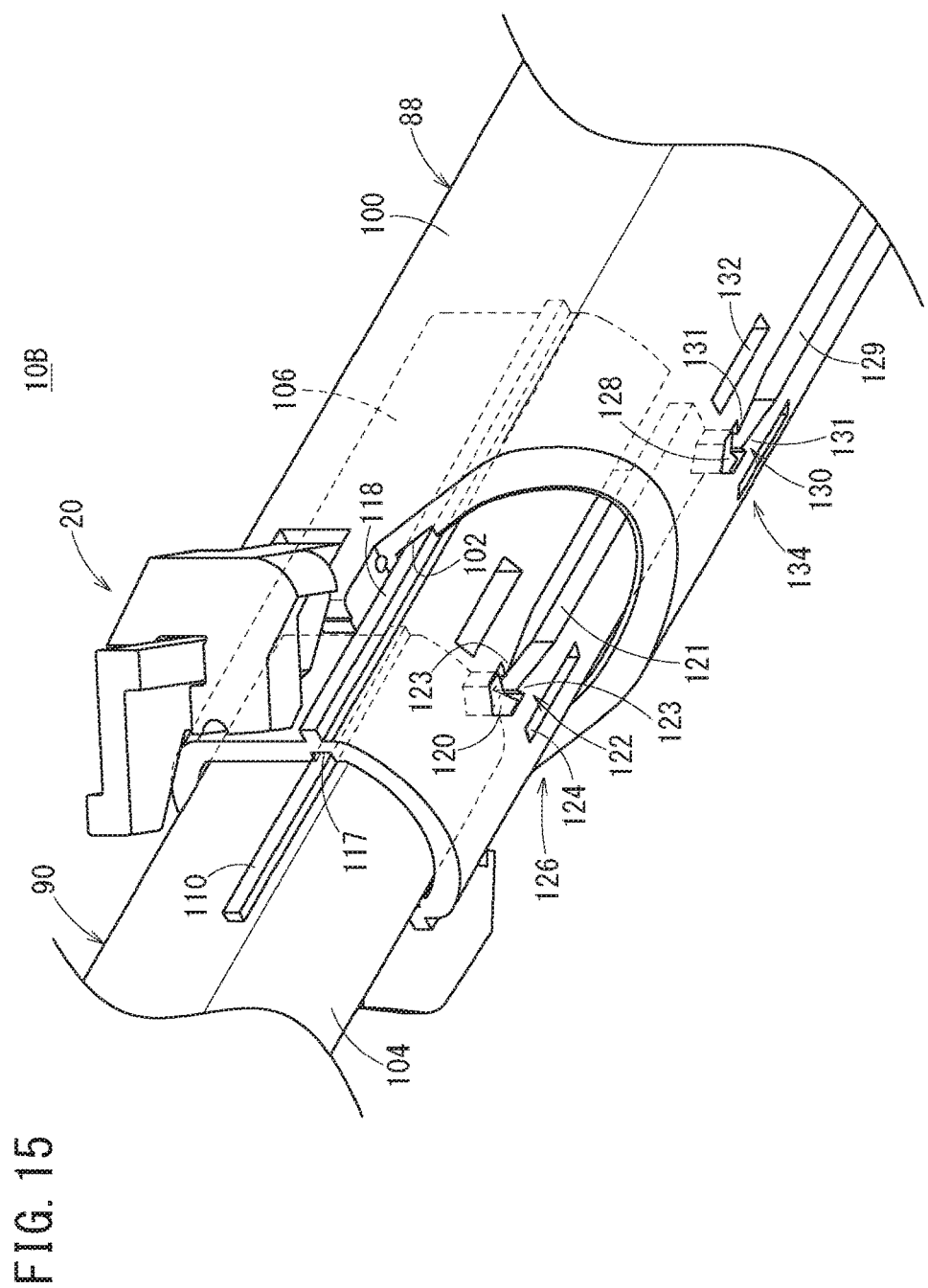
FIG. 15 is a perspective view of the catheter assembly illustrated in FIG. 11 from the rear side in a state where a first engaging portion and a first engaging protrusion have engaged with each other and a second engaging portion and a second engaging protrusion have engaged with each other.

As illustrated in FIG. 12, an outer surface of a base end portion of the inner tube 104 can include a first engaging protrusion 120 protruding outward (downward in the illustrated example) provided thereon. Meanwhile, as illustrated in FIGS. 14 and 15, the outer tube 106 can include a first passage 121 extending in the axial direction and allowing the first engaging protrusion 120 to be displaced in the axial direction, and a first engaging portion 122 disposed on the side of a lead end of the first passage 121, provided thereon. The first passage 121 extends to a base end surface of the outer tube 106. In the initial state of the catheter assembly 10B, the first engaging protrusion 120 is positioned at a base end of the first passage 121. According to the present embodiment, the first passage 121 is a hole passing through the inside and the outside of the outer tube 106, but may be a groove provided on an inner surface of the outer tube 106.

The first engaging portion 122 has a pair of pawls 123 protruding into the first passage 121. A slit long hole 124 extending in the axial direction of the outer tube 106, is provided on each of the left and right outsides of the pair of pawls 123. Accordingly, the pair of pawls 123 is elastically deformable in directions in which the pair of pawls 123 comes close to and separates from each other. The first engaging portion 122 including the above configuration can mutually engage the first engaging protrusion 120 provided on the inner tube 104.

As illustrated in FIGS. 14 and 15, when the inner tube 104 relatively moves forward to a predetermined position with respect to the outer tube 106, the first engaging portion 122 and the first engaging protrusion 120 engage with each other. Specifically, the first engaging portion 122 gets over the pair of pawls 123 and the pair of pawls 123 hooks on both sides of a base end of the first engaging protrusion 120. A state where the first engaging portion 122 and the first engaging protrusion 120 have engaged with each other, helps prevent a relative movement in the axial direction between the inner tube 104 and the outer tube 106. Therefore, the inner tube 104 is prevented from coming off the outer tube 106 to the leading end side. In addition, the inner tube 104 is prevented from moving backward into the outer tube 106.

In this manner, a first locking mechanism 126 for preventing relative displacement in the axial direction between the inner tube 104 and the outer tube 106 in a state where the protector 90 has covered the needlepoint 87, can include the first engaging portion 122 and the first engaging protrusion 120. Note that even in a case where bending stress has acted on the inner tube 104 and the outer tube 106, engaging action between the rail protrusions 110 provided on an outer surface of the inner tube 104 and the rail grooves 117 provided on the inner surface of the outer tube 106, helps prevent the first engaging protrusion 120 from coming off the first engaging portion 122. Accordingly, the function of the first locking mechanism 126 can be preferably retained.

As illustrated in FIGS. 14 and 15, an outer surface of a base end portion of the outer tube 106 can include a second engaging protrusion 128 protruding outward (downward in the illustrated example) provided thereon. Meanwhile, the needle hub 88 (specifically, the extension portion 100) can include a second passage 129 extending in the axial direction and allowing displacement in the axial direction of the second engaging protrusion 128 provided on the outer tube 106, and a second engaging portion 130 disposed on the side of a leading end of the second passage 129, provided thereon. The second passage 129 extends to a base end surface of the needle hub 88. In the initial state of the catheter assembly 10B, the second engaging protrusion 128 is positioned at a base end of the second passage 129. According to the present embodiment, the second passage 129 is a hole passing through the inside and the outside of the needle hub 88, but may be a groove provided on an inner surface of the needle hub 88.

The second engaging portion 130 has a pair of pawls 131 protruding into the second passage 129. A slit long hole 132 extending in the axial direction of the needle hub 88, is provided on each of the left and right outsides of the pair of pawls 131. Accordingly, the pair of pawls 131 is elastically deformable in directions in which the pair of pawls 131 comes close to and separates from each other. The second engaging portion 130 including the above configuration can mutually engage the second engaging protrusion 128 provided on the inner tube 104.

As illustrated in FIGS. 14 and 15, when the outer tube 106 relatively moves forward to a predetermined position with respect to the needle hub 88, the second engaging portion 130 and the second engaging protrusion 128 engage with each other. Specifically, the second engaging protrusion 128 gets over the pair of pawls 131 and the pair of pawls 131 hooks on both sides of a base end of the second engaging protrusion 128. A state where the second engaging portion 130 and the second engaging protrusion 128 have engaged with each other, helps prevent relative displacement in the axial direction between the outer tube 106 and the needle hub 88. Therefore, the outer tube 106 is prevented from coming off the needle hub 88. In addition, the outer tube 106 is prevented from moving backward into the needle hub 88.

In this manner, a second locking mechanism 134 for preventing the relative movement in the axial direction between the outer tube 106 and the needle hub 88 in a state where the protector 90 has covered the needlepoint 87, can include the second engaging portion 130 and the second engaging protrusion 128. Note that even in a case where bending stress has acted on the outer tube 106 and the needle hub 88, engaging action between the rail protrusions 118 provided on an outer surface of the outer tube 106 and the rail grooves 102 provided on the inner surface of the needle hub 88, helps prevent the second engaging protrusion 128 from coming off the second engaging portion 130. Accordingly, the function of the second locking mechanism 134 can be preferably retained.

As illustrated in FIG. 14, the first locking mechanism 126 and the second locking mechanism 134 are disposed so as to be shifted to each other in a circumferential direction.

The needle support portion 20 according to the second embodiment has a configuration similar to that of the needle support portion 20 according to the first embodiment. That is, in the initial state of the catheter assembly 10B, the needle support portion 20 supports the inner needle 86 through the catheter 82 on the leading end side beyond the catheter hub 84. The needle support portion 20 can be movable with respect to the needle hub 88 in order to change from a first state of supporting the inner needle 86 to a second state of releasing the support with respect to the inner needle 86 and allowing the catheter hub 84 to pass. In the initial state, a coupling portion between each of the pair of support arms 42 and the extension portion 100, is positioned on the leading end side beyond the base end of the catheter hub 84. A leading end of the needle hub 88 (a leading end of the extension portion 100) and each of the support arms 42 are coupled so as to be rotatable through a hinge structure 48 similar to that according to the first embodiment.

A restraining portion 44 according to the second embodiment has a configuration similar to that of the restraining portion 44 according to the first embodiment. The restraining portion 44 is pressed by the catheter hub 84 in accordance with a forward movement of the catheter hub 84 so that the restraint with respect to the pair of the support arms 42 is released.

Note that the respective members in the catheter assembly 10B according to the second embodiment, having the same terms as those in the catheter assembly 10A according to the first embodiment, include the materials exemplified as constituent materials of those of the catheter assembly 10A.

The catheter assembly 10B according to the second embodiment is basically constituted as described above. Functions and effects of the catheter assembly 10B will be described below.

As illustrated in FIGS. 11 and 13, the catheter assembly 10B in the initial state is in a state to be described below. The inner needle 86 has been inserted into the catheter 82 and the needlepoint 87 has protruded from the leading end of the catheter 82 by the predetermined length. The leading end fitting portion 108 of the inner tube 104 has been inserted into the base end of the catheter hub 84. The outer tube 106 has maximally moved to the leading end side in a movable range with respect to the inner tube 104. The catheter 82 and the inner needle 86 have been exposed from the leading end of the needle hub 88, and the catheter hub 84 and the protector 90 have been housed in the needle hub 88. The protector 90 is positioned on the base end side in the needle hub 88. The restraining portion 44 has been positioned at the backward position in a movable range. The pair of support arms 42 has been restrained in the closed state by the restraining portion 44. The inner needle 86 has been held by the pair of support arms 42 in the closed state through the catheter 82.

In the use of the catheter assembly 10B, a user (for example, a medical doctor or a nurse) grips the needle hub 88 and punctures a blood vessel of a patient with the catheter 82 and the inner needle 86. In this case, the inner needle 86 has been supported by a support hole 54 formed between the pair of support arms 42 that has been closed, through the catheter 82, so that the deflection of the inner needle 86 is inhibited upon the puncture. Accordingly, a stable puncture can be performed.

After the puncture, a finger hooks the pair of wings 94 protruding from the needle hub 88, and presses the pair of wings 94 in the leading end direction. Accordingly, the catheter hub 84 and the catheter 82 that have been coupled to the pair of wings 94, move in the leading end direction with respect to the needle hub 88. Thus, an insertion length of the catheter 82 into the blood vessel increases. Meanwhile, the protector 90 coupled to the catheter hub 84 also moves forward in the needle hub 88 in accordance with the forward movement operation of the wings 94.

As illustrated in FIGS. 16A and 16B, the catheter hub 84 presses the restraining portion 44 in the leading end direction in accordance with the forward movement of the catheter hub 84. Accordingly, the restraining portion 44 moves in the leading end direction with respect to the pair of support arms 42, and the second restraining protrusion 58b separates from the second engaging groove 56b. The second restraining protrusion 58b separates from the second engaging groove 56b so that the restraint of the restraining portion 44 with respect to the pair of support arms 42 is released and the pair of support arms 42 becomes expansible. After that, the pair of support arms 42 is pressed from the rear side by the catheter hub 84 and expands in accordance with a further forward movement of the catheter hub 84.

After the catheter 82 has been inserted into the blood vessel by a predetermined length, the needle hub 88 is next pulled in the base end direction in a state where a position of the catheter member 98 has been held. Accordingly, the inner needle 86 moves in the base end direction in the catheter 82, the catheter hub 84, and the protector 90. In this case, since the leading end fitting portion 108 of the inner tube 104 of the protector 90 and the catheter hub 84 have fitted to each other due to predetermined fitting force, the protector 90 extends in accordance with the backward movement of the needle hub 88. Specifically, the inner tube 104 relatively moves to the side of a leading end of the outer tube 106 and the outer tube 106 also relatively moves to the side of the leading end of the needle hub 88. After a while, a state where the protector 90 has maximally extended is acquired (refer to FIGS. 17A and 17B). During a process during which the protector 90 maximally extends, the inner needle 86 is evulsed from the catheter 82. In addition, the inner needle 86 is housed in the protector 90 with the needlepoint 87.

In a state where the protector 90 has maximally extended, as illustrated in FIGS. 14 and 15, a function of the first locking mechanism 126 helps prevent the relative movement in the axial direction between the inner tube 104 and the outer tube 106. In addition, a function of the second locking mechanism 134 helps prevent the relative movement in the axial direction between the outer tube 106 and the needle hub 88.

Specifically, in the first locking mechanism 126, since the first engaging protrusion 120 has been positioned at the maximum leading end position of the first passage 121, the inner tube 104 cannot move any further in the leading end direction with respect to the outer tube 106. In the first locking mechanism 126, since the first engaging protrusion 120 and the first engaging portion 122 has engaged with each other, the inner tube 104 cannot move in the base end direction with respect to the outer tube 106.

In the second locking mechanism 134, since the second engaging protrusion 128 has been positioned at the maximum leading end position of the second passage 129, the outer tube 106 cannot move any further in the leading end direction with respect to the needle hub 88. In the second locking mechanism 134, since the second engaging protrusion 128 and the second engaging portion 130 have engaged with each other, the outer tube 106 cannot move in the base end direction with respect to the needle hub 88.

Figure 17A:
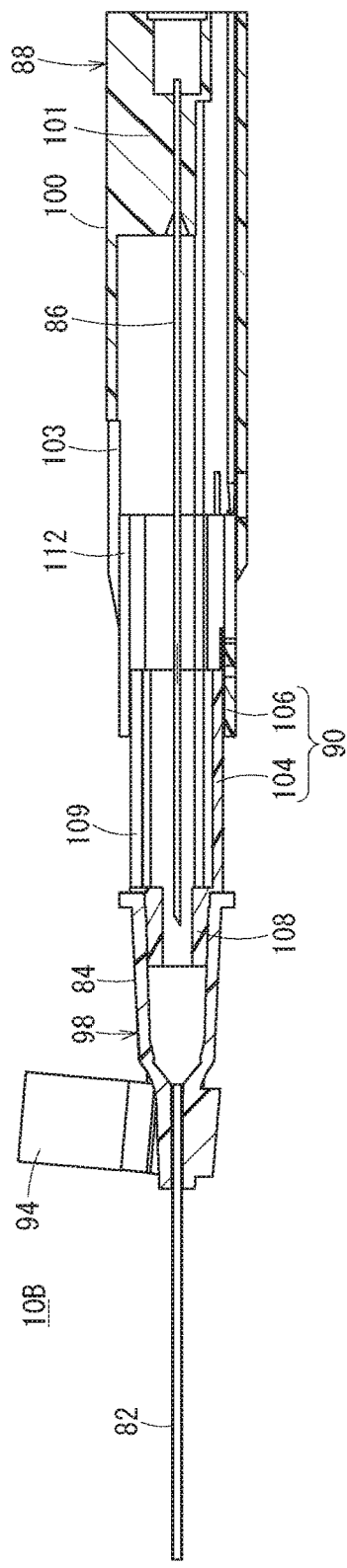
FIG. 17A is a longitudinal-sectional view of the catheter assembly illustrated in FIG. 11 in a state where a protector has maximally extended.
Figure 17B:
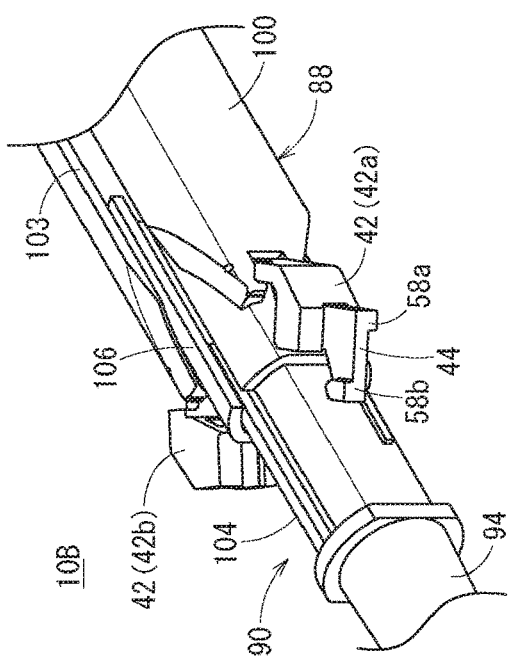
FIG. 17B is a perspective view of the catheter assembly illustrated in FIG. 11 in the state where the protector has maximally extended.

During a process during which the catheter assembly 10B is transferred from a state in FIG. 16A to a state in FIG. 17A, the pair of support arms 42 is pressed from the rear side by the catheter hub 84 so as to expand and allow movements of the catheter hub 84 and the protector 90 with respect to the needle hub 88 (refer to FIG. 17B). In this manner, the needle support portion 20 supports the inner needle 86 in the initial state and inhibits the deflection of the inner needle 86 upon the puncture. Meanwhile, after the puncture, the pair of support arms 42 opens so as to prevent interference with the catheter hub 84 and the protector 90.

After the protector 90 has maximally extended, when the needle hub 88 is further pulled in the base end direction with respect to the catheter member 98, as illustrated in FIG. 18, the fit between the catheter hub 84 and the leading end fitting portion 108 of the inner tube 104 comes off. Accordingly, a state where the protector 90 has completely separated from the catheter member 98 and only the catheter member 98 out of the catheter assembly 10B has been detained on the side of the patient, can be acquired.

After the catheter member 98 and the protector 90 have separated from each other, the pair of wings 94 provided on the catheter hub 84 expands in the left and right direction. The pair of wings 94 is fixed to skin of the patient with a tape or the like so as to fix the catheter hub 84. A connector of a transfusion tube, not illustrated, can be coupled to the side of the base end of the catheter hub 84, and supply of a transfusion material (a medical fluid) to the patient through the transfusion tube can be performed.

As described above, the catheter assembly 10B according to the second embodiment is capable of inhibiting the deflection of the inner needle 86 upon a puncture and performing a stable puncture since the pair of support arms 42 supports the inner needle 86 upon the puncture. According to the second embodiment, other respective constituent portions shared with the first embodiment acquire functions and effects similar to those according to the first embodiment.

According to the second embodiment, in the initial state, the catheter hub 84 has been housed in the needle hub 88 (refer to FIG. 11). Accordingly, an exposure length of the inner needle 86 from the needle hub 88 included in the housing can be shortened in comparison to a conventional catheter assembly having a protector. Therefore, an entire length of the catheter assembly 10B in the initial state, namely, a length from the base end of the needle hub 88 to a leading end of the inner needle 86 can be made shorter than a conventional catheter assembly having a protector. Accordingly, excellent storage due to its compactness can be acquired and the puncture operation can be performed relatively easily. Since the exposure length of the inner needle 86 from the needle hub 88 is short, the protector 90 may be also made to be short. Accordingly, an entire product length even in a state where the protector 90 has covered the needlepoint 87 (a needlepoint protecting state), can be relatively short. Therefore, the waste is compact, and disposal is relatively easy to perform.

Furthermore, according to the second embodiment, since the pair of wings 94 functions as the operating portion for the catheter hub 84 in the initial state, there is no need for providing an exclusive operating portion to the catheter hub 84. Thus, the configuration can be relatively simplified.

Note that, the catheter assembly 10B may adopt the needle support portions 20a to 20c illustrated in FIGS. 7A to 8, respectively, instead of the needle support portion 20. The catheter assembly 10B may adopt the hinge structures 48a and 48b illustrated in FIGS. 9A to 9C instead of the hinge structure 48. The catheter assembly 10B may adopt support holes 54a to 54d illustrated in FIGS. 10A to 10D, respectively, instead of the support hole 54.

In the above configuration, the catheter hub 84 presses the restraining portion 44 so that the restraint with respect to the pair of support arms 42 is released. Instead of this type of configuration, the wings 94 may press the restraining portion 44, and the restraint with respect to the pair of support arms 42 may be released. Alternatively, the catheter assembly 10B may further include a guide wire G inserted into the inner needle 86, and a guide wire operating portion 64 for operating the guide wire G, the guide wire operating portion 64 being coupled to the guide wire G (refer to FIG. 13). In this case, the guide wire operating portion 64 may press the restraining portion 44 in accordance with a forward movement of the guide wire operating portion 64. Thus, the restraint with respect to the pair of support arms 42 may be released.

Figure 19:
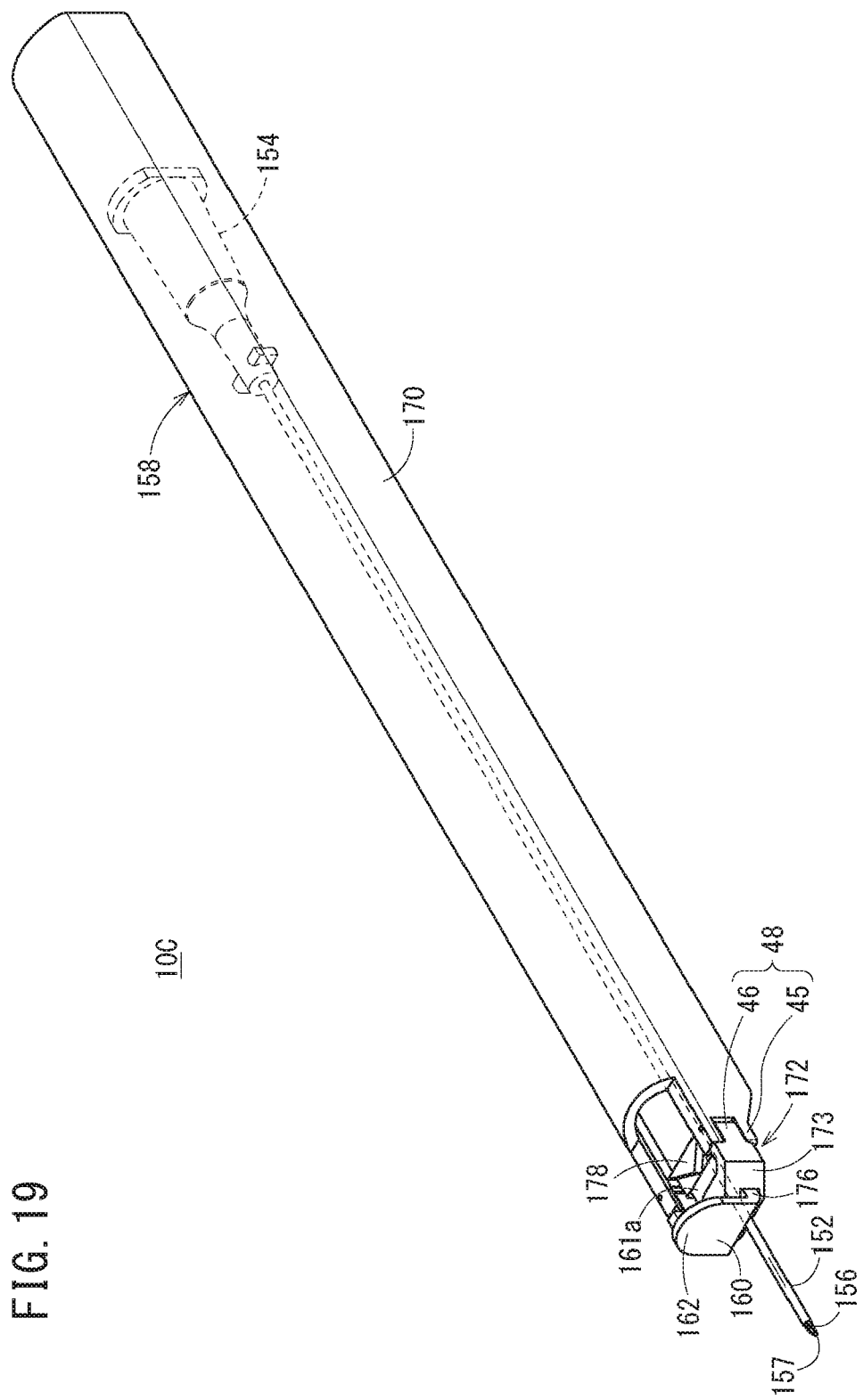
FIG. 19 is a perspective view of a catheter assembly according to a third embodiment of the present disclosure.
Figure 20:
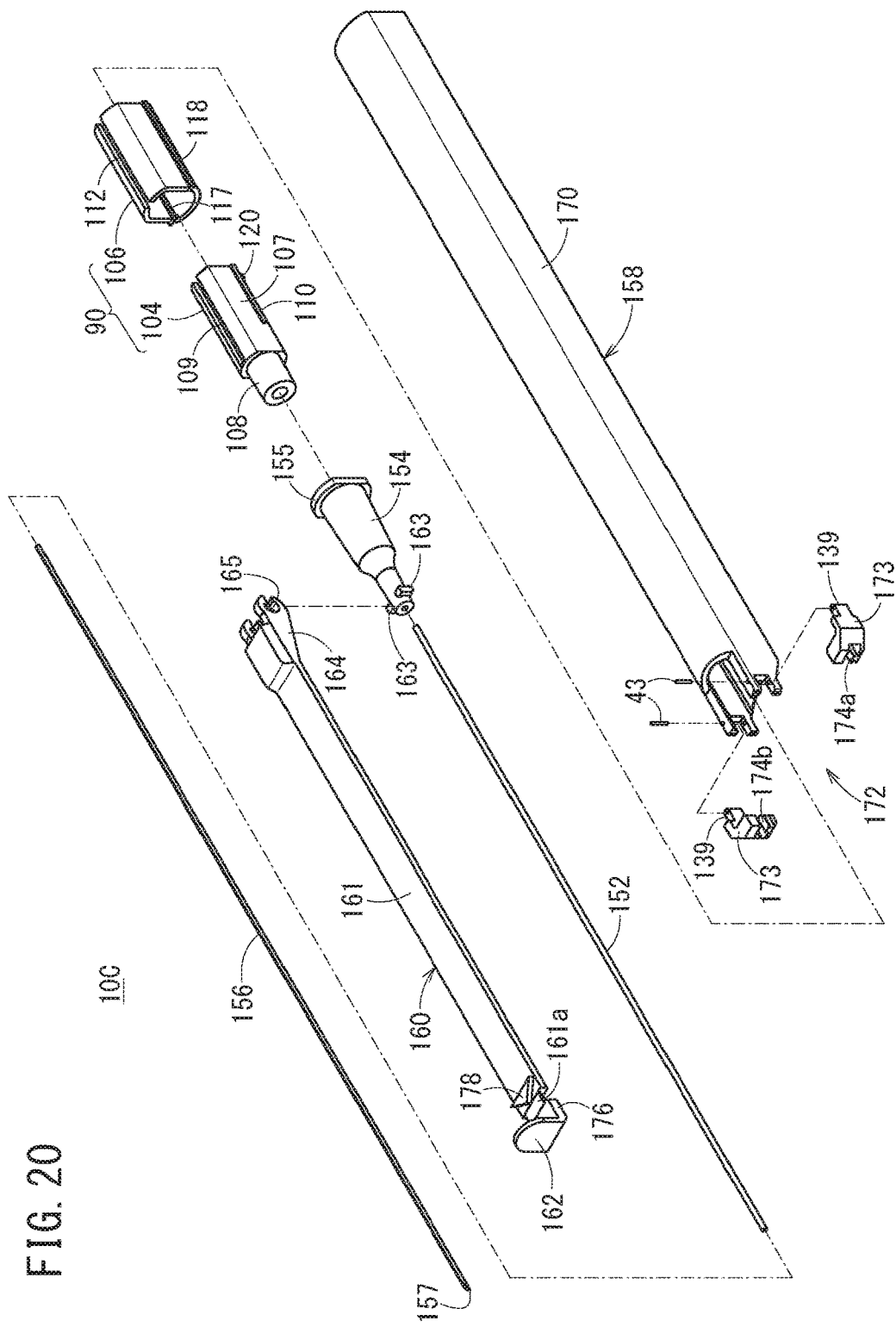
FIG. 20 is an exploded perspective view of the catheter assembly illustrated in FIG. 19.
Figure 21:
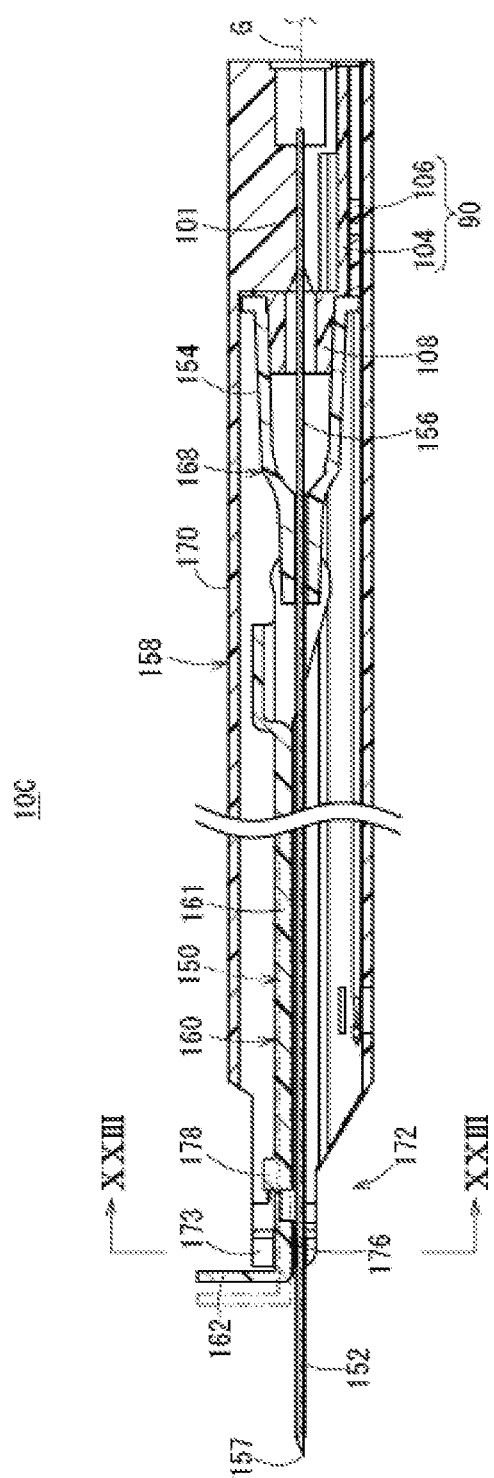
FIG. 21 is a partially omitted longitudinal-sectional view of the catheter assembly illustrated in FIG. 19.

FIG. 19 is a perspective view of a catheter assembly 10C according to a third embodiment of the present disclosure. FIG. 20 is an exploded perspective view of the catheter assembly 10C. FIG. 21 is a partially omitted longitudinal-sectional view of the catheter assembly 10C. Note that, in the catheter assembly 10C according to the third embodiment, elements having functions and effects the same as or similar to those of the catheter assembly 10B according to the second embodiment, are denoted with the same reference signs, and the duplicate descriptions thereof will be omitted.

The catheter assembly 10C can include a tubular catheter 152 having flexibility, a catheter hub 154 coupled to the side of a base end of the catheter 152, a tubular inner needle 156 having a sharp needlepoint 157 on a leading end and insertable into the inside of the catheter 152, a needle hub 158 coupled to the inner needle 156, a protector 90 that covers the needlepoint 157 of the inner needle 156 when the inner needle 156 is evulsed, and a needle support portion 172 for inhibiting deflection of the inner needle 156 upon a puncture.

A user (for example, a medical doctor or a nurse) grips and operates the needle hub 158 so that a leading end portion of the catheter assembly 10C punctures a blood vessel of a patient. The catheter assembly 10C has a double tubular structure in which the inner needle 156 has been inserted into the catheter 152 and the inner needle 156 has protruded from a leading end of the catheter 152 by a predetermined length in an initial state before use (before a puncture to the patient). In the initial state of the catheter assembly 10C, the side of a base end of the catheter hub 154 and the side of a leading end of the needle hub 158 have been coupled through a protector 90.

The catheter assembly 10C in the initial state can include one assembly having the double tubular structure of the catheter 152 and the inner needle 156, the catheter hub 154, the protector 90, and the needle hub 158 combined, and is integrally operable.

The catheter 152 according to the third embodiment is longer than the catheters 12 and 82 according to the first and second embodiments, respectively. The catheter 152 may be used as a catheter, for example, a central venous catheter, a PICC, or a midline catheter, longer than a peripheral venous catheter in length. Note that the catheter 152 may be used as the peripheral venous catheter.

The hollow cylindrical catheter hub 154 is coupled and fixed to a base end of the catheter 152. A flange portion 155 protruding outward and extending in a circumferential direction, is provided on a base end of the catheter hub 154.

The catheter hub 154 is provided with a hub operating portion 160 for operating the catheter hub 154. In the initial state of the catheter assembly 10C, at least a part of the hub operating portion 160 has been exposed from the needle hub 158. Specifically, in the initial state, the hub operating portion 160 extends along the inner needle 156 and the catheter hub 154. In addition, a base end portion is coupled to the catheter hub 154, and a leading end portion is exposed on the side of the leading end of the needle hub 158.

The hub operating portion 160 has a long main body portion 161 and a tab 162 to be hooked by a finger, the tab 162 being provided at a leading end of the main body portion 161. The tab 162 protrudes upward from the leading end of the main body portion 161.

The hub operating portion 160 is coupled to the catheter hub 154 so as to be rotatable. In the present illustrated example, a support protrusion 163 protruding outward is provided on an outer surface on each of the left and right sides of the catheter hub 154. Each of the support protrusions 163 extends in an upper and lower direction. Meanwhile, a base end portion of the main body portion 161 can include a pair of coupling pieces 164 each having a coupling groove 165 and facing each other on the left and right sides, provided thereon.

Figure 22A:
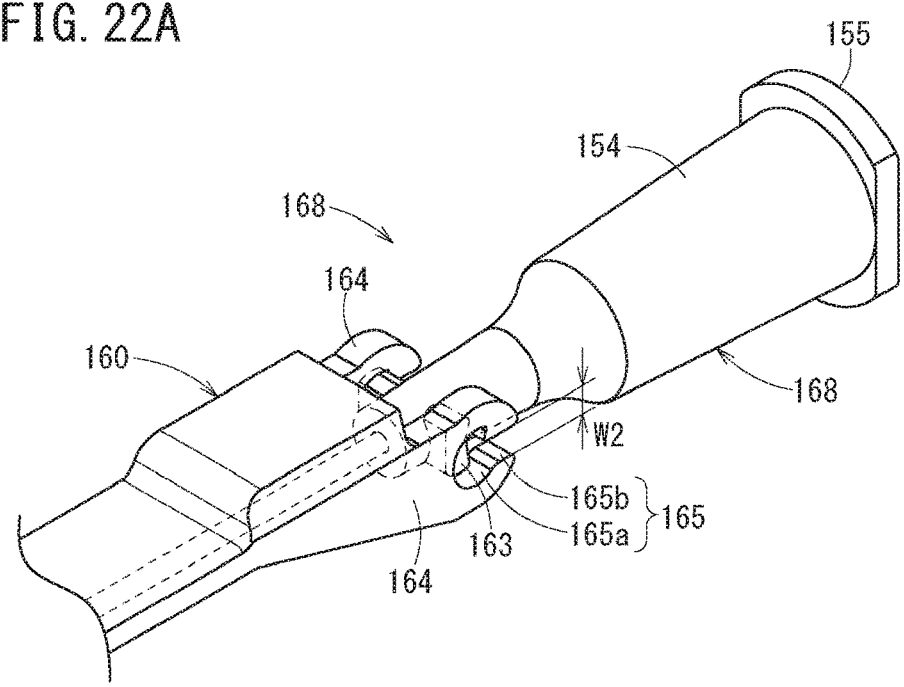
FIG. 22A is a perspective view of a coupling state between a catheter hub and a hub operating portion.

As illustrated in FIG. 22A, each of the coupling grooves 165 can include a first groove 165a for engagement and a second groove 165b for separation having a groove width narrower than the first groove 165a, extending from the first groove 165a in a base end direction, and reaching a base end surface of the coupling piece 164. The groove width W2 of the second grooves 165b is slightly larger than a width W1 of the support protrusions 163 (refer to FIG. 22B). Each of the support protrusions 163 provided to the catheter hub 154 is inserted into each of the first grooves 165a provided to the hub operating portion 160. Accordingly, the hub operating portion 160 has the support protrusions 163 as axial portions and is supported so as to be rotatable with respect to the catheter hub 154. In the initial state, the hub operating portion 160 is substantially parallel to the catheter 152 and the inner needle 156, and each of the support protrusions 163 engages with each of the first grooves 165a. Thus, the hub operating portion 160 can be prevented from separating from the catheter hub 154.

Figure 22B:
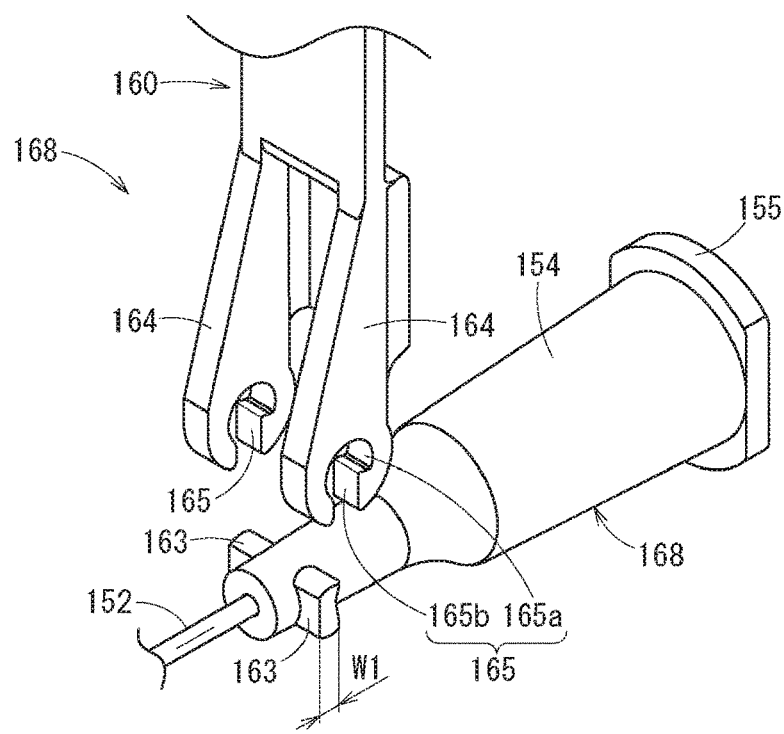
FIG. 22B is a perspective view of a separating state between the catheter hub and the hub operating portion.

As illustrated in FIG. 22B, since extending directions of the support protrusions 163 and the second grooves 165b become the same at a position at which the hub operating portion 160 is substantially perpendicular to an axial direction of the catheter hub 154, the hub operating portion 160 is separable from the catheter hub 154. Note that a constituent material of the hub operating portion 160 is not particularly limited, and may be the same as a constituent material of the catheter hub 154, for example.

Hereinafter, a member including the catheter 152, the catheter hub 154, and the hub operating portion 160, will be referred to as a "catheter member 168".

As illustrated in FIG. 21, the inner needle 156 is formed sufficiently longer than the catheter 152. In the initial state of the catheter assembly 10C, the needlepoint 157 protrudes from a leading end opening of the catheter 152 by a predetermined length. The inner needle 156 according to the third embodiment is longer than the inner needles 16 and 86 according to the first and second embodiments, respectively.

In the initial state of the catheter assembly 10C, the inner needle 156 has a midway part in the longitudinal direction inserted into the inside of the catheter hub 154, and has the side of the base end held inside the needle hub 158.

The needle hub 158 has an inner needle holding portion 101 holding the base end of the inner needle 156, and an extension portion 170 protruding in a leading end direction beyond the catheter hub 154. The extension portion 170 is included in a housing that houses the catheter hub 154 and the protector 90 in the initial state. In the initial state, a coupling portion between each of the pair of support arms 173 and the extension portion 170, is positioned on the leading end side beyond the base end of the catheter hub 154. The extension portion 170 according to the third embodiment is longer than the extension portion 100 according to the second embodiment.

In the initial state of the catheter assembly 10C, the catheter 152 and the inner needle 156 are exposed from the leading end of the needle hub 158, and the catheter hub 154 and the protector 90 are housed in the needle hub 158. As a result, the leading end of the needle hub 158 protrudes to a midway of the catheter 152. According to the present embodiment, a position of the base end of the catheter hub 154 is positioned on the base end side beyond a position of the center in an axial direction of the needle hub 158, and the leading end of the needle hub 158 is positioned on the leading end side beyond a position of the center in a longitudinal direction of the catheter 152.

In the initial state of the catheter assembly 10C, a majority of the hub operating portion 160 is housed in the needle hub 158, and the leading end portion of the hub operating portion 160 (tab 162) is exposed on the leading end side beyond the leading end of the needle hub 158.

Figure 26:
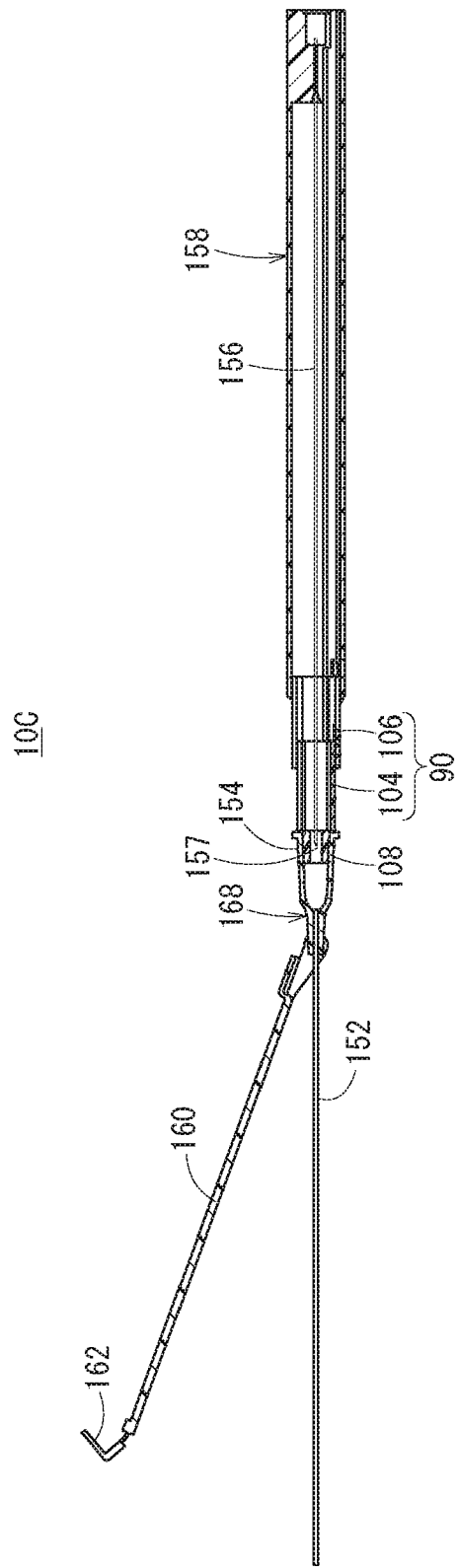
FIG. 26 is a longitudinal-sectional view of a state where the hub operating portion has further moved forward from the state of FIG. 25 and a protector has maximally extended.

The protector 90 houses the inner needle 156 upon evulsion of the inner needle 156 from the catheter 152 so as to cover the needlepoint 157 of the inner needle 156. The protector 90 according to the third embodiment has a configuration similar to that of the protector 90 according to the second embodiment, and has an inner tube 104 and an outer tube 106. In the initial state, a leading end fitting portion 108 of the inner tube 104 fits to the inside of the base end of the catheter hub 154. Upon an evulsion operation of the inner needle 156 from the catheter 152, the protector 90 extends with the needle hub 158 so as to cover an entire length of the inner needle 156 (refer to FIG. 26). Note that the catheter assembly 10C also can include the first locking mechanism 126 and the second locking mechanism 134 illustrated in FIG. 15.

As illustrated in FIGS. 19 and 21, the needle support portion 172 supports the inner needle 156 through a catheter 152 on the leading end side beyond the catheter hub 154 in the initial state. The needle support portion 172 is provided movable with respect to the needle hub 158 in order to change from a first state of supporting the inner needle 156 to a second state of releasing the support with respect to the inner needle 156 and allowing the catheter hub 154 to pass.

According to the third embodiment, specifically, the needle support portion 172 has the pair of support arms 173 openable and closeable and a restraining portion 176 capable of restraining the pair of support arms 173 in a closed state and also releasing the restraint.

The pair of support arms 173 is rotably coupled to the extension portion 170 through a pair of support pins 43. In the initial state, the coupling portion between each of the pair of support arms 173 and the extension portion 170, is positioned on the leading end side beyond the base end of the catheter hub 154.

In the present illustrated example, each of the pair of support pins 43 has an axis in an upper and lower direction. The pair of support arms 173 supported by the pair of support pins 43 is openable and closeable in a left and right direction. One of the support arms 173 has a bending engaging groove 174a provided thereon and the other has a bending engaging groove 174b provided thereon when viewed from the front side in the closed state. Each of the engaging grooves 174a and 174b passes through each of the support arms 173 in a longitudinal direction.

In the present illustrated example, the one engaging groove 174a (hereinafter, referred to as a "first engaging groove 174a") and the other engaging groove 174b (hereinafter, referred to as a "second engaging groove 174b) both bend downward. Note that the first engaging groove 174a and the second engaging groove 174b both may bend upward. Alternatively, one may bend upward and the other may bend downward.

A configuration of the pair of support arms 173 according to the third embodiment is similar to the pair of support arms 42 according to the first embodiment except the first engaging groove 174a and the second engaging groove 174b. The leading end of the needle hub 158 (a leading end of the extension portion 170) and each of the support arms 173 are coupled so as to be rotatable through a hinge structure 48 the same as in the first embodiment.

The restraining portion 176 is slidable with respect to the pair of support arms 173, and is formed as a part of the above hub operating portion 160. The restraining portion 176 moves forward in accordance with a forward movement of the hub operating portion 160 so that the restraint with respect to the pair of support arms 173 is released.

Figure 23:
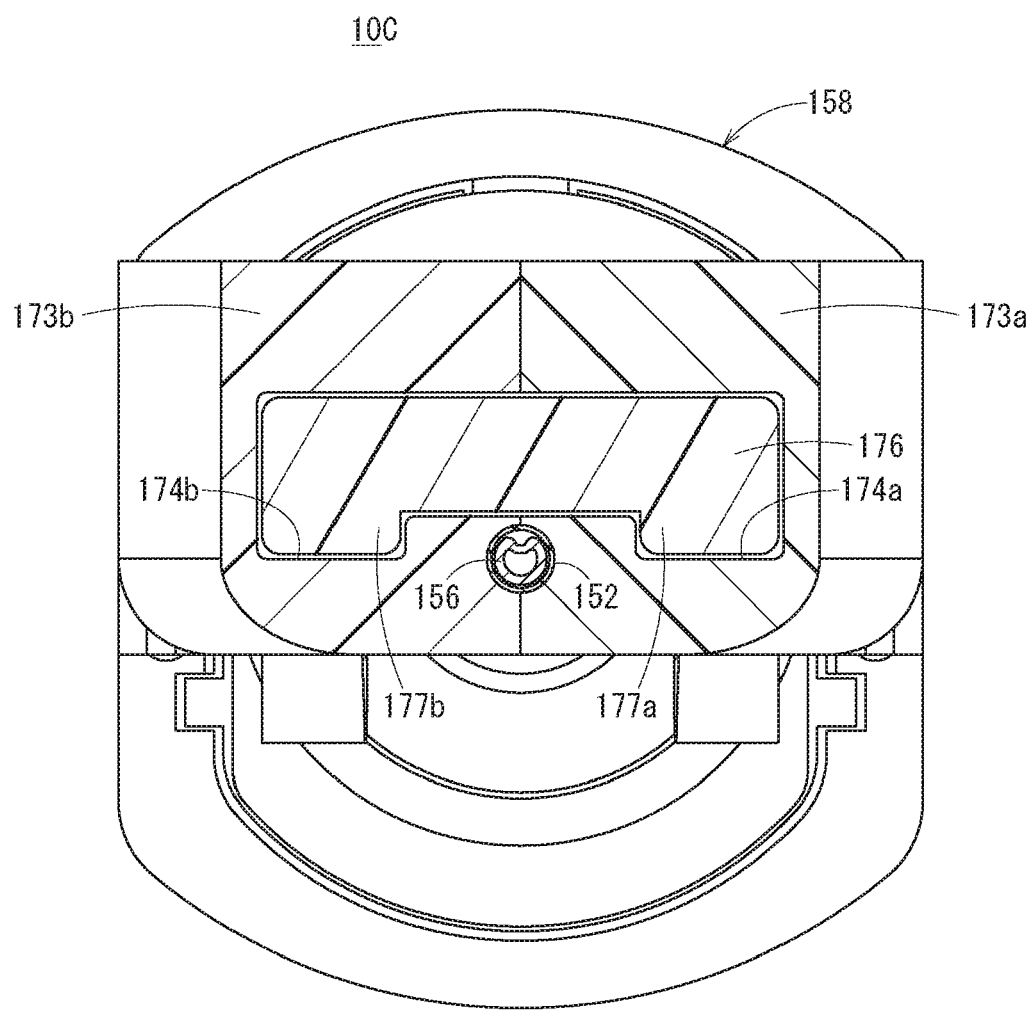
FIG. 23 is a cross-sectional view taken along line XXIII-XXIII of FIG. 21.

Specifically, the restraining portion 176 is provided at a leading end of the main body portion 161 of the hub operating portion 160. FIG. 23 is a cross-sectional view taken along line XXIII-XXIII of FIG. 21. As illustrated in FIG. 23, the restraining portion 176 has a first restraining protrusion 177a engaging with the first engaging groove 174a so as to be slidable and a second restraining protrusion 177b engaging with the second engaging groove 174b so as to be slidable.

In the present illustrated example, the first restraining protrusion 177a and the second restraining protrusion 177b protrude in the same direction so as to adapt to shapes of the first engaging groove 174a and the second engaging groove 174b provided on the pair of support arms 173, respectively. When the restraining portion 176 is positioned at an initial position (backward position), the first restraining protrusion 177a and the second restraining protrusion 177b of the restraining portion 176 engage with the first engaging groove 174a and the second engaging groove 174b of the pair of support arms 173, respectively. Thus, the pair of support arms 173 is restrained in a closed state.

In accordance with a movement of the restraining portion 176 in the leading end direction, the first restraining protrusion 177a and the second restraining protrusion 177b separate from the first engaging groove 174a and the second engaging groove 174b of the pair of support arms 173 in the leading end direction, respectively. When the first restraining protrusion 177a and the second restraining protrusion 177b separate from the first engaging groove 174a and the second engaging groove 174b, respectively, the restraint of the restraining portion 176 with respect to the pair of support arms 173 is released. Then, the pair of support arms 173 becomes expansible.

As illustrated in FIGS. 19 and 20, the hub operating portion 160 can include a protrusion for expansion 178 for opening the pair of support arms 173, provided slightly on the base end side beyond the restraining portion 176. The protrusion for expansion 178 is formed so as to be tapered and be triangular in the present illustrated example.

Note that the respective members in the catheter assembly 10C according to the third embodiment, having the same terms as those in the catheter assemblies 10A and 10B according to the first and second embodiments, include the materials exemplified as constituent materials of those of the catheter assemblies 10A and 10B.

The catheter assembly 10C according to the third embodiment is basically constituted as described above. Functions and effects of the catheter assembly 10C will be described below.

As illustrated in FIGS. 19 and 21, the catheter assembly 10C in the initial state is in a state to be described below. The inner needle 156 has been inserted into the catheter 152 and the needlepoint 157 has protruded from the leading end of the catheter 152 by the predetermined length. The leading end fitting portion 108 of the inner tube 104 has been inserted into the base end of the catheter hub 154. The outer tube 106 has maximally moved to the leading end side in a movable range with respect to the inner tube 104. The catheter 152 and the inner needle 156 have been exposed from the leading end of the needle hub 158, and the catheter hub 154 and the protector 90 have been housed in the needle hub 158. The protector 90 is positioned on the base end side in the needle hub 158. The restraining portion 176 has been positioned at the backward position in a movable range. The pair of support arms 173 has been restrained in the closed state by the restraining portion 176. The inner needle 156 has been held by the pair of support arms 173 in the closed state through the catheter 152.

In the use of the catheter assembly 10C, a user (for example, a medical doctor or a nurse) grips the needle hub 158 and punctures a blood vessel of a patient with the catheter 152 and the inner needle 156. In this case, a portion close to the leading end of the needle hub 158 is gripped so that the needlepoint 157 becomes stable and the puncture operation is performed relatively easily. Upon the puncture, the pair of support arms 173 that has been closed supports the inner needle 156 through the catheter 152. Thus, the deflection of the inner needle 156 upon the puncture is inhibited or prevented. Accordingly, a stable puncture can be performed.

After the puncture, a finger hooks the tab 162 provided at a leading end of the hub operating portion 160, and presses the tab 162 in the leading end direction. In this case, a finger of a hand (for example, an index finger) that has gripped the part close to the leading end of the needle hub 158, can operate the tab 162. Thus, transition from the operation of the puncture to the operation of the tab 162 is promptly performed.

When the tab 162 is pressed in the leading end portion, the restraining portion 176 provided on the hub operating portion 160 moves in the leading end direction with respect to the pair of support arms 173. Then, the first restraining protrusion 177a and the second restraining protrusion 177b separate from the first engaging groove 174a and the second engaging groove 174b, respectively. Due to the separation, the restraint of the restraining portion 176 with respect to the pair of support arms 173 is released. Then, the pair of support arms 173 becomes expansible.

Figure 24A:
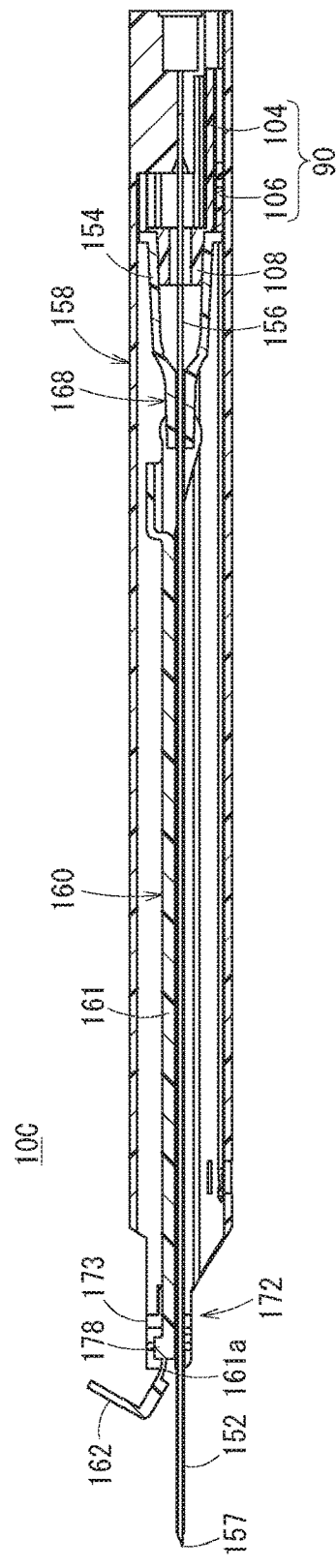
FIG. 24A is a longitudinal-sectional view of the catheter assembly illustrated in FIG. 19 in a state where the hub operating portion has moved slightly forward.
Figure 24B:
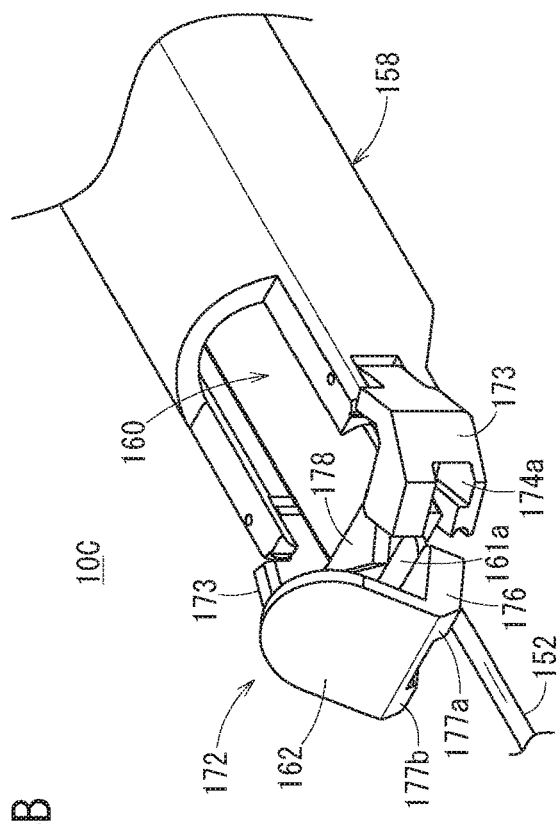
FIG. 24B is a perspective view of a part of the catheter assembly in the state of FIG. 24A.

As illustrated in FIGS. 24A and 24B, when the hub operating portion 160 further moves forward, the pair of support arms 173 is pressed from the rear side by the protrusion for expansion 178 so as to expand. In this case, the leading end portion of the hub operating portion 160 is flexible at a part of a thin-walled portion 161a. Thus, the leading end of the hub operating portion 160 can be prevented from interfering with skin of the patient.

Next, as illustrated in FIG. 25, when the hub operating portion 160 further moves forward, the catheter hub 154 and catheter 152 that have been coupled to the hub operating portion 160 further move in the leading end direction with respect to the needle hub 158. Thus, an insertion length of the catheter 152 into the blood vessel increases. Meanwhile, the protector 90 coupled to the catheter hub 154 also moves forward in the needle hub 158 in accordance with the forward movement of the hub operating portion 160.

When the catheter 152 has been inserted into the blood vessel by a predetermined length, next, the needle hub 158 is pulled in the base end direction with respect to the catheter member 168. Accordingly, the inner needle 156 moves in the base end direction in the catheter 152, the catheter hub 154, and the protector 90. In this case, since the leading end fitting portion 108 of the inner tube 104 of the protector 90 and the catheter hub 154 have fitted to each other due to predetermined fitting force, the protector 90 extends in accordance with the backward movement of the needle hub 158. Specifically, the inner tube 104 moves to the side of a leading end of the outer tube 106. In addition, the outer tube 106 moves to the side of the leading end of the needle hub 158. Accordingly, a state where the protector 90 has maximally extended, is acquired (refer to FIG. 26). During a process during which the protector 90 maximally extends, the inner needle 156 is evulsed from the catheter 152 and the inner needle 156 is also housed in the protector 90 with the needlepoint 157.

In a state where the protector 90 has maximally extended, a function of the first locking mechanism 126 prevents movements in the axial direction of the inner tube 104 and the outer tube 106. In addition, a function of the second locking mechanism 134 prevents movements in the axial direction of the outer tube 106 and the needle hub 158.

Figure 27:
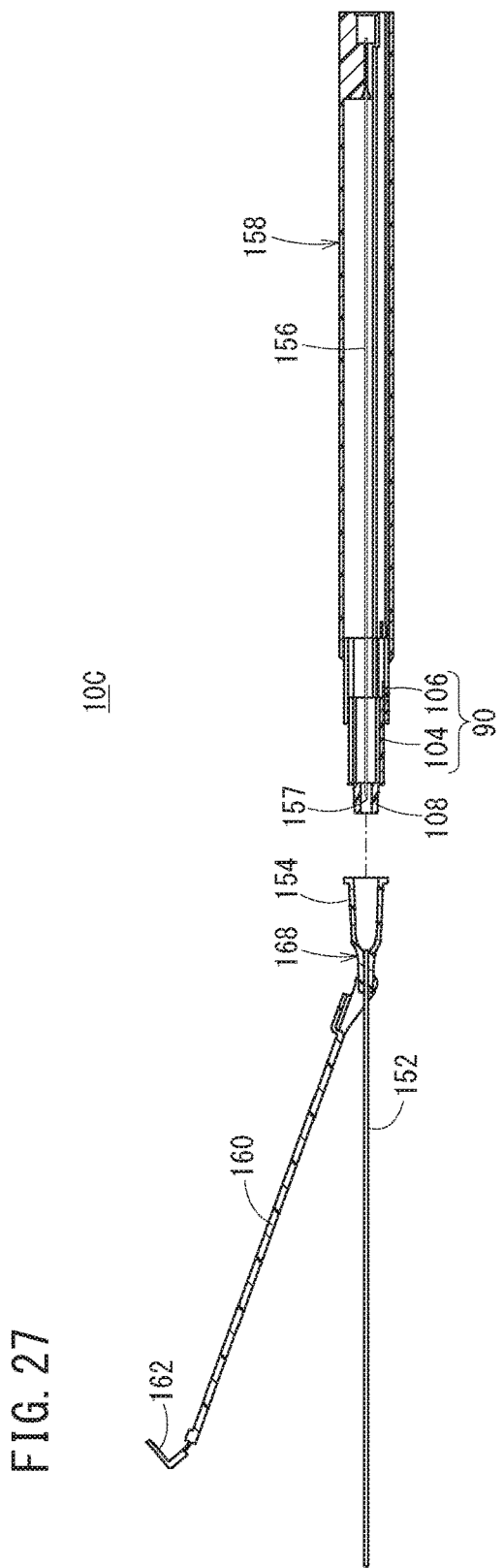
FIG. 27 is a longitudinal-sectional view of the catheter assembly illustrated in FIG. 19 in a state where a catheter member and the protector have separated from each other.

After the protector 90 has maximally extended, when the needle hub 158 is further pulled in the base end direction with respect to the catheter member 168, as illustrated in FIG. 27, the fit between the catheter hub 154 and the leading end fitting portion 108 of the inner tube 104 comes off. Accordingly, a state where the protector 90 has completely separated from the catheter member 168 and only the catheter member 168 out of the catheter assembly 10C has been detained on the side of the patient, is acquired.

After the catheter member 168 and the protector 90 have separated from each other, the hub operating portion 160 separates from the catheter hub 154. Specifically, in a state where the hub operating portion 160 has risen so as to be in a position substantially perpendicular to the catheter hub 154, the hub operating portion 160 is pulled upward so that the hub operating portion 160 separates from the catheter hub 154 (refer to FIG. 22B). After that, the catheter hub 154 is fixed to the skin of the patient with a dressing material or a tape. A connector of a transfusion tube, not illustrated, is coupled to the side of the base end of the catheter hub 154, and supply of a transfusion material (a medical fluid) to the patient through the transfusion tube is performed.

As described above, the catheter assembly 10C according to the third embodiment is capable of inhibiting the deflection of the inner needle 156 upon a puncture and performing a stable puncture since the pair of support arms 173 supports the inner needle 156 upon the puncture as in the first and second embodiments. As in the second embodiment, since the catheter hub 154 has been housed in the needle hub 158 in the initial state, an entire product length can be shortened in both of the initial state and the needlepoint protecting state due to the protector 90. According to the third embodiment, other respective constituent portions shared with the first and second embodiments acquire functions and effects similar to those according to the first and second embodiments.

According to the third embodiment, in the initial state, the hub operating portion 160 extends along the inner needle 156 and the catheter hub 154. In addition, the base end portion is coupled to the catheter hub 154 and the leading end portion is exposed on the side of the leading end of the needle hub 158. With this configuration, a portion of the hub operating portion 160 that has been exposed on the side of the leading end of the needle hub 158 is touched so that the operation with respect to the hub operating portion 160 can be performed. Thus, the same hand that grips the side of the leading end of the needle hub 158 upon a puncture, can operate the hub operating portion 160. Accordingly, the same hand can perform the puncture operation and the forward movement operation of the catheter 152. Thus, excellent operability can be acquired.

According to the third embodiment, the restraining portion 176 is provided as a part of the hub operating portion 160, and the restraint with respect to the pair of support arms 173 is released upon the forward movement of the hub operating portion 160. With this configuration, the restraint with respect to the pair of support arms 173 is automatically released in response to the forward movement of the catheter hub 154 based on the operation with respect to the hub operating portion 160. Thus, there is no need for an independent release operation, and excellent operability is acquired.

Note that the catheter assembly 10C may adopt the support arms 65, 66, and 68 illustrated in FIGS. 7A to 8, respectively, instead of the support arms 173. The catheter assembly 10C may adopt the hinge structures 48a and 48b illustrated in FIGS. 9A to 9C instead of the hinge structure 48. The catheter assembly 10C may adopt the support holes 54a to 54d illustrated in FIGS. 10A to 10D, respectively, instead of the support hole 54.

The catheter assembly 10C may further include a guide wire G inserted into the inner needle 156, and a guide wire operating portion 150 for operating the guide wire G, the guide wire operating portion 150 being coupled to the guide wire G (refer to FIG. 21). In this case, the restraining portion 176 may be provided as a part of the guide wire operating portion 150. In accordance with a forward movement of the guide wire operating portion 150, the guide wire operating portion 150 may press the restraining portion 176 so that the restraint with respect to the pair of support arms 173 may be released.

The detailed description above describes a catheter assembly. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter assembly comprising:
a catheter;
a catheter hub fixed to a base end portion of the catheter;
an inner needle having a needlepoint, inserted into the catheter;
a needle hub coupled to the inner needle;
a needle support portion for supporting the inner needle through the catheter on a leading end side of the catheter and distally of the catheter hub;
the needle support portion having a pair of support arms openable and closeable in a lateral direction, and a restraining portion capable of restraining the pair of support arms in a closed state and releasing a restraint of the pair of support arms;
the needle hub has an extension portion extending axially and distally of the catheter hub;
a coupling portion between each of the pair of support arms and the extension portion is positioned on the leading end side of the catheter and distally of a base end of the catheter hub; and
wherein the restraining portion is movable with the respect to the pair of support arms by a distal movement of the catheter hub relative to the inner needle, which releases the restraint with respect to the pair of support arms.

2. The catheter assembly according to claim 1, further comprising:
a bending first engaging groove provided in one of the pair of support arms;
a bending second engaging groove provided in another of the pair of support arms;
a first restraining protrusion capable of engaging with the first engaging groove, provided on the restraining portion; and
a second restraining protrusion capable of engaging with the second engaging groove, provided on the restraining portion.

3. The catheter assembly according to claim 2,
wherein when the restraining portion is positioned at a first position, the first restraining protrusion engages with the first engaging groove and the second restraining protrusion engages with the second engaging groove; and
when the restraining portion is positioned at a second position, the first restraining portion separates form the first engage groove and the second restraining protrusion separates from the second engaging groove.

4. The catheter assembly according to claim 3,
wherein the second restraining protrusion protrudes to a side opposite to a side on which the inner needle is present.

5. The catheter assembly according to claim 1,
wherein the extension portion and each of the support arms are coupled so as to be rotatable through a hinge structure having a first structure and a second structure;
the first structure is provided on one of the extension portions and each of the support arms, and has a plurality of coupling pieces facing each other and a recess portion formed between the plurality of coupling pieces; and
the second structure is provided on another of the extension portion and each of the support arms, and has a coupling protruding portion disposed in the recess portion.

6. The catheter assembly according to claim 5,
wherein a support hole for supporting the inner needle is formed between the pair of support arms in the closed state; and
a contact surface between the pair of support arms is shifted in the lateral direction with respect to a center of the inner needle supported by the support hole.

7. The catheter assembly according to claim 1,
wherein the restraining portion is slidable with respect to the pair of support arms.

8. The catheter assembly according to claim 1,
wherein the restraining portion is provided as a part of a hub operating portion for operating the catheter hub.

9. A catheter assembly comprising:
a catheter;
a catheter hub fixed to a base end portion of the catheter;
an inner needle having a needlepoint, inserted into the catheter;
a needle hub coupled to the inner needle, the needle hub having an extension portion extending axially and distally of the catheter hub;
a needle support portion for supporting the inner needle through the catheter on a leading end side of the catheter and distally of the catheter hub, the needle support portion having a pair of rotatable support arms, and a restraining portion capable of restraining the pair of support arms;
a coupling portion between each of the pair of support arms and the extension portion is positioned on the leading end side of the catheter and distally of a base end of the catheter hub; and
wherein the restraining portion is movable with the respect to the pair of support arms by a distal movement of the catheter hub relative to the inner needle, which releases the restraint with respect to the pair of support arms.

10. The catheter assembly according to claim 9, comprising:
a bending first engaging groove provided in one of the pair of support arms;
a bending second engaging groove provided in another of the pair of support arms;
a first restraining protrusion capable of engaging with the first engaging groove, provided on the restraining portion; and
a second restraining protrusion capable of engaging with the second engaging groove, provided on the restraining portion.

11. The catheter assembly according to claim 10,
wherein when the restraining portion is positioned at a first position, the first restraining protrusion engages with the first engaging groove and the second restraining protrusion engages with the second engaging groove; and
when the restraining portion is positioned at a second position, the first restraining protrusion separates from the first engaging groove and the second restraining protrusion separates from the second engaging groove.

12. The catheter assembly according to claim 11,
wherein the second restraining protrusion protrudes to a side opposite to a side on which the inner needle is present.

13. The catheter assembly according to claim 9,
wherein the extension portion and each of the support arms are coupled so as to be rotatable through a hinge structure having a first structure and a second structure;
the first structure is provided on one of the extension portions and each of the support arms, and has a plurality of coupling pieces facing each other and a recess portion formed between the plurality of coupling pieces;
the second structure is provided on another of the extension portion and each of the support arms, and has a coupling protruding portion disposed in the recess portion;
wherein a support hole for supporting the inner needle is formed between the pair of support arms in the closed state; and
a contact surface between the pair of support arms is shifted in the lateral direction with respect to a center of the inner needle supported by the support hole.

14. The catheter assembly according to claim 9,
wherein the restraining portion is slidable with respect to the pair of support arms.

15. The catheter assembly according to claim 9,
wherein the restraining portion is provided as a part of a hub operating portion for operating the catheter hub.

16. A catheter assembly comprising:
a catheter;
a catheter hub fixed to a base end portion of the catheter;
an inner needle having a needlepoint, inserted into the catheter;
a needle hub coupled to the inner needle, the needle hub having an extension portion extending axially and distally of the catheter hub;
a needle support portion for supporting the inner needle through the catheter on a leading end side of the catheter and distally of the catheter hub, the needle support portion having a pair of support arms openable and closeable in a lateral direction, and a restraining portion capable of restraining the pair of support arms;
a hub operating portion coupled to the catheter hub, and the pair of support arms being laterally disposed between the restraining portion; and
wherein the restraining portion is movable with the respect to the pair of support arms by a distal movement of the hub operating portion relative to the inner needle, which releases the restraint with respect to the pair of support arms.

* * * * *